(12) United States Patent
Du et al.

(10) Patent No.: US 11,512,057 B2
(45) Date of Patent: Nov. 29, 2022

(54) UNSATURATED HYDROCARBON PYRIMIDINE THIOETHER COMPOUNDS AND PREPARATION METHOD AND APPLICATION THEREOF

(71) Applicant: Zhejiang University of Technology, Zhejiang (CN)

(72) Inventors: Xiaohua Du, Zhejiang (CN); Shulin Hao, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 297 days.

(21) Appl. No.: 16/615,080

(22) PCT Filed: Nov. 5, 2018

(86) PCT No.: PCT/CN2018/113891
§ 371 (c)(1),
(2) Date: Nov. 19, 2019

(87) PCT Pub. No.: WO2019/165798
PCT Pub. Date: Sep. 6, 2019

(65) Prior Publication Data
US 2020/0207723 A1 Jul. 2, 2020

(30) Foreign Application Priority Data

Feb. 27, 2018 (CN) .......................... 201810160958.5

(51) Int. Cl.
*C07D 239/56* (2006.01)
*A01N 43/54* (2006.01)

(52) U.S. Cl.
CPC ........... *C07D 239/56* (2013.01); *A01N 43/54* (2013.01)

(58) Field of Classification Search
None
See application file for complete search history.

(56) References Cited

U.S. PATENT DOCUMENTS

| 4,723,034 | A | 2/1988 | Schirmer et al. |
| 5,106,852 | A | 4/1992 | Schuetz et al. |
| 5,378,711 | A | 1/1995 | Schuetz et al. |
| 5,416,068 | A | 5/1995 | Grammenos et al. |
| 5,554,578 | A | 9/1996 | Wenderoth et al. |
| 5,935,965 | A | 8/1999 | Kirstgen et al. |
| 6,114,342 | A | 9/2000 | Oberdorf et al. |
| 2006/0235057 | A1 | 10/2006 | Bit et al. |

FOREIGN PATENT DOCUMENTS

| CN | 101311170 A | 11/2008 |
| CN | 101875639 A | 11/2010 |
| EP | 0242081 A1 | 10/1987 |
| EP | 0299694 A2 | 1/1989 |
| EP | 0335519 A1 | 10/1989 |

*Primary Examiner* — Savitha M Rao
*Assistant Examiner* — Gregg Polansky
(74) *Attorney, Agent, or Firm* — Muncy, Geissler, Olds & Lowe, P.C.

(57) ABSTRACT

The present invention discloses unsaturated hydrocarbon pyrimidine thioether compounds of formula (I) and preparation method and application thereof, the compounds of formula (I) exhibit high insecticidal and acaricidal activity against adults, larvae and eggs of harmful mites and insects in the agriculture, civil use and animal technology fields, meanwhile, the compounds also exhibit good bactericidal activity, and can be widely applied as an insecticide, an acaricide and/or a bactericide in agriculture or other fields

10 Claims, No Drawings

UNSATURATED HYDROCARBON PYRIMIDINE THIOETHER COMPOUNDS AND PREPARATION METHOD AND APPLICATION THEREOF

TECHNICAL FIELD

The present invention belongs to the fields of agricultural insecticides, acaricides and bactericides. Specifically, it relates to unsaturated hydrocarbon pyrimidine thioether compounds and preparation method and application thereof.

BACKGROUND ART

Researchers have found that methoxy acrylate compounds have biological activity long ago. The compounds have been reported to have insecticidal and acaricidal activity as described in the following literatures: EP2420811/EP299694/EP3:35519/US20060235075/CN 101311170, etc. In addition, the pyrimidine methoxy acrylate compounds have been also reported as an insecticide, an acaricide or a bactericide:

The patent U.S. 005106852 relates to compounds of the following general formula as insecticides:

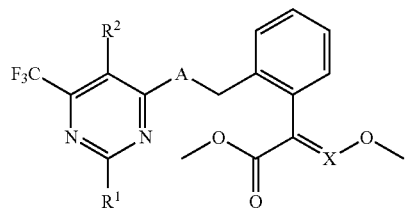

The patent U.S. 005378711 relates to compounds of the following general formula as bactericides:

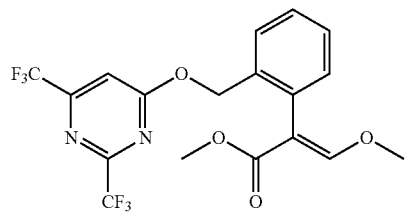

The patent U.S. 00593565 relates to compounds of the following general formula as acaricides and bactericides:

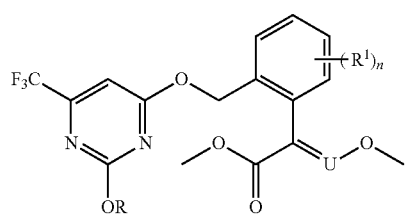

The patent U.S. 006114342 relates to compounds of the following general formula as insecticides and bactericides:

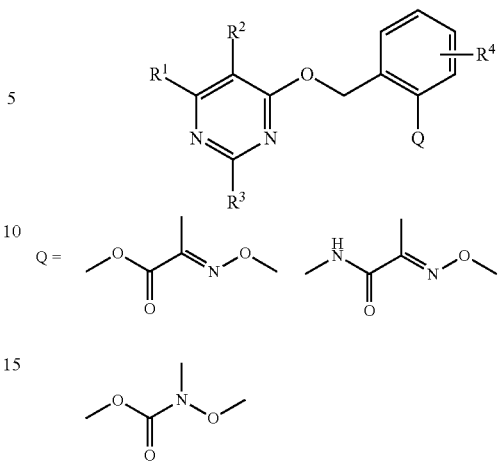

The patent CN 101311170 relates to compounds of the following general formula as insecticides and bactericides:

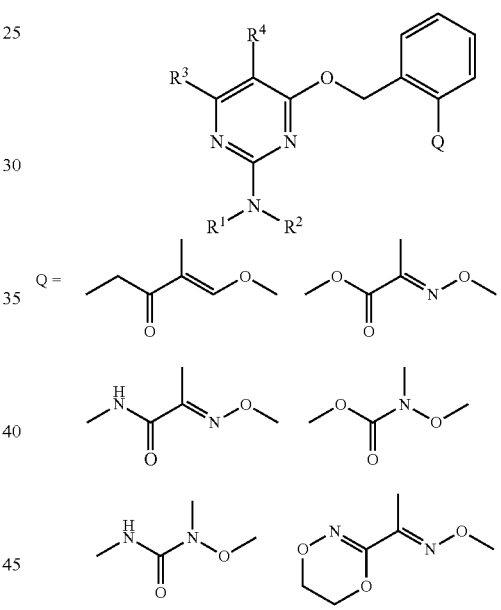

However, in many cases, effects of the compounds described in these literatures on animal pests are not satisfactory.

Moreover, unsaturated hydrocarbon pyrimidine thioether compounds of the general formula (I) in the present invention have not been reported.

SUMMARY OF THE INVENTION

The present invention aims to provide unsaturated hydrocarbon pyrimidine thioether compounds and preparation method thereof. The compounds have improved performance in the aspect of preventing harmful fungi, animal pests and mites, especially in the aspect of preventing fungi, insects, nematodes and mites, especially in the aspect of preventing fungi, insects and mites.

In order to achieve the above objects, the technical solution of the present invention is as follows:

The present invention provides substituted pyrimidine thioether compounds of formula (I):

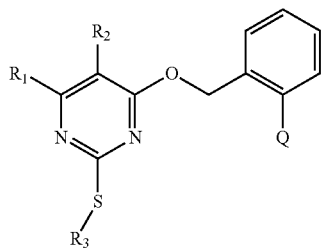

I

In formula (I):

$R_1$ is selected from the group consisting of hydrogen, halogen, $C_1$-$C_{12}$ alkyl, $C_3$-$C_{12}$ cycloalkyl, halogenated $C_1$-$C_{12}$ alkyl, $C_2$-$C_{12}$ alkenyl, halogenated $C_2$-$C_{12}$ alkenyl, $C_2$-$C_{12}$ alkynyl, halogenated $C_2$-$C_{12}$ alkynyl, $C_1$-$C_{12}$ alkoxy and $C_2$-$C_{12}$ alkenyloxy;

$R_2$ is selected from the group consisting of hydrogen, halogen, nitro, cyano, $C_1$-$C_{12}$ alkyl, halogenated $C_1$-$C_{12}$ alkyl, $C_2$-$C_{12}$ alkenyl, halogenated $C_2$-$C_{12}$ alkenyl, $C_2$-$C_{12}$ alkynyl, halogenated $C_2$-$C_{12}$ alkynyl, $C_1$-$C_{12}$ alkoxy, $C_1$-$C_{12}$ alkyl thiol, $C_1$-$C_{12}$ alkyl SO, $C_1$-$C_{12}$ alkyl $SO_2$, halogenated di($C_1$-$C_{12}$ alkyl thiol, halogenated $C_1$-$C_{12}$ alkyl SO, halogenated $C_1$-$C_{12}$ alkyl $SO_2$, $C_1$-$C_{12}$ alkylamino, di($C_1$-$C_{12}$ alkyl) amino and $C_1$-$C_{12}$ alkylcarbonyl;

$R_3$ is selected from the group consisting of $C_2$-$C_{12}$ alkenyl, halogenated $C_2$-$C_{12}$ alkenyl, $C_2$-$C_{12}$ alkynyl, halogenated $C_2$-$C_{12}$ alkynyl, $C_3$-$C_{12}$ cycloalkenyl, heteroarylmethylene and arylmethylene, wherein the arylmethylene or heteroarylmethylene is arylmethylene or heteroarylmethylene which is unsubstituted or whose H are substituted by n $R_4$ groups;

wherein $R_4$ is one or more groups selected from the group consisting of hydrogen, halogen, hydroxyl, sulfhydryl, amino, CN, $NO_2$, $C_1$-$C_{12}$ alkyl, halogenated $C_1$-$C_{12}$ alkyl, $C_3$-$C_8$ cycloalkyl, $C_2$-$C_{12}$ alkenyl, halogenated $C_2$-$C_{12}$ alkenyl, $C_2$-$C_{12}$ alkynyl, halogenated $C_2$-$C_{12}$ alkynyl, $C_1$-$C_{12}$ alkylamino, di($C_1$-$C_{12}$ alkyl) amino, halogenated $C_1$-$C_{12}$ alkylamino, $C_1$-$C_{12}$ alkoxy, halogenated $C_1$-$C_{12}$ alkoxy, $C_1$-$C_{12}$ alkylthio, halogenated $C_1$-$C_{12}$ alkylthio, $C_2$-$C_{12}$ alkenyloxy, halogenated $C_2$-$C_{12}$ alkenyloxy, $C_2$-$C_{12}$ alkynyloxy, halogenated $C_2$-$C_{12}$ alkynyloxy, $C_1$-$C_{12}$ alkylcarbonyl, halogenated $C_1$-$C_{12}$ alkylcarbonyl, $C_1$-$C_{12}$ alkylsulfinyl, halogenated $C_1$-$C_{12}$ alkylsulfinyl, $C_1$-$C_{12}$ alkylsulfonyl, halogenated $C_1$-$C_{12}$ alkylsulfonyl, $C_1$-$C_{12}$ alkylcarbonyloxy, $C_1$-$C_{12}$ alkylcarbonylamino, $C_1$-$C_{12}$ alkylsulfonyloxy, $C_1$-$C_{12}$ alkoxycarbonyl, $C_1$-$C_{12}$ alkoxy $C_1$-$C_{12}$ alkoxy, $C_1$-$C_{12}$ alkoxycarbonyl $C_1$-$C_{12}$ alkyl, $C_1$-$C_{12}$ alkoxycarbonylamino, $C_1$-$C_{12}$ alkoxycarbonyl $C_1$-$C_{12}$ alkoxy, aryl, heteroaryl, aryloxy, heteroaryloxy, aralkyloxy, heteroarylalkyloxy, arylamino and heteroarylamine, wherein the aryl, heteroaryl, aryloxy, heteroaryloxy, aralkyloxy, heteroarylalkyloxy, aralkyloxy or heteroarylalkyloxy is aryl, heteroaryl, aryloxy, heteroaryloxy, aralkyloxy, heteroarylalkyloxy, arylamino or heteroarylamine which is each independently unsubstituted or whose H are substituted by 1-4 following groups: halogen, CN, $NO_2$, $C_1$-$C_{12}$ alkyl, $C_1$-$C_{12}$ haloalkyl, $C_1$-$C_{12}$ haloalkoxy, $C_1$-$C_{12}$ alkoxy, $C_1$-$C_{12}$ alkoxycarbonyl or $C_1$-$C_{12}$ alkylsulfonyl;

n is an integer selected from 0 to 5;

and Q is a group selected from $Q_1$-$Q_{14}$ (including stereoisomers):

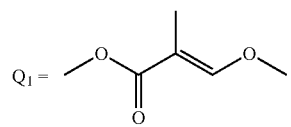
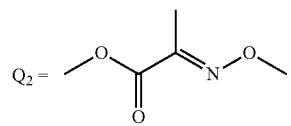
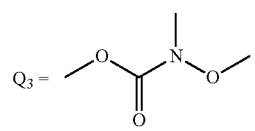
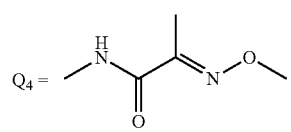
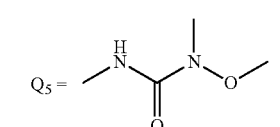
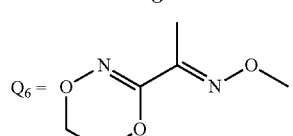
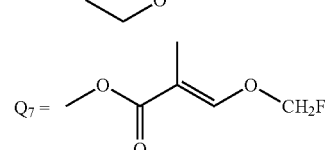
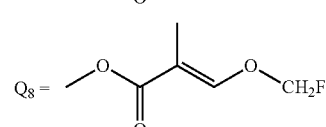
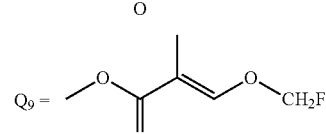
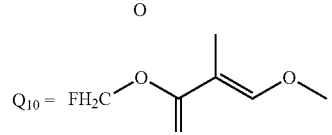
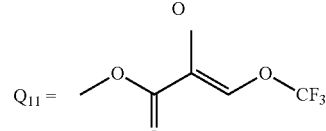
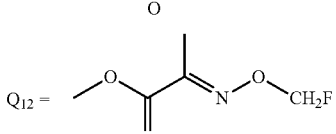
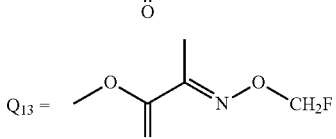

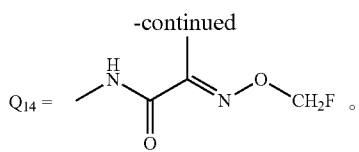

Preferred are compounds of formula (I), wherein $R_1$ is selected from the group consisting of hydrogen, halogen, $C_1$-$C_6$ alkyl, $C_3$-$C_8$ cycloalkyl, halogenated $C_1$-$C_6$ alkyl, $C_2$-$C_6$ alkenyl, halogenated $C_2$-$C_6$ alkenyl, $C_2$-$C_6$ alkynyl, halogenated $C_2$-$C_6$ alkynyl, $C_1$-$C_6$ alkoxy and $C_2$-$C_6$ alkenyloxy;

$R_2$ is selected from the group consisting of hydrogen, halogen, nitro, cyano, $C_1$-$C_6$ alkyl, halogenated $C_1$-$C_6$ alkyl, $C_2$-$C_6$ alkenyl, halogenated $C_2$-$C_6$ alkenyl, $C_2$-$C_6$ alkynyl, halogenated $C_2$-$C_6$ alkynyl, $C_1$-$C_6$ alkoxy, $C_1$-$C_6$ alkyl thiol, $C_1$-$C_6$ alkyl $SO_2$, $C_6$ alkyl halogenated $C_1$-$C_6$ alkyl thiol, halogenated $C_1$-$C_6$ alkyl SO, halogenated $C_1$-$C_6$ alkyl $SO_2$, $C_1$-$C_6$ alkylamino, di($C_1$-$C_6$ alkyl)amino and $C_1$-$C_6$ alkylcarbonyl;

$R_3$ is selected from the group consisting of $C_2$-$C_6$ alkenyl, halogenated $C_2$-$C_6$ alkenyl, $C_2$-$C_6$ alkynyl, halogenated $C_2$-$C_6$ alkynyl, $C_3$-$C_6$ cycloalkenyl, arylmethylene and heteroarylmethylene, wherein the arylmethylene or heteroarylmethylene is arylmethylene or heteroarylmethylene which is unsubstituted or whose H is substituted by n $R_4$ groups;

wherein $R_4$ is one or more groups selected from the group consisting of hydrogen, halogen, hydroxyl, sulfhydryl, amino, CN, $NO_2$, $C_1$-$C_6$ alkyl, halogenated $C_1$-$C_6$ alkyl, $C_3$-$C_8$ cycloalkyl, $C_2$-$C_6$ alkenyl, halogenated $C_2$-$C_6$ alkenyl, $C_2$-$C_6$ alkynyl, halogenated $C_2$-$C_6$ alkynyl, $C_1$-$C_6$ alkylamino, di($C_1$-$C_6$ alkyl) amino, halogenated $C_1$-$C_6$ alkylamino, $C_1$-$C_6$ alkoxy, halogenated $C_1$-$C_6$ alkoxy, $C_1$-$C_6$ alkylthio, halogenated $C_1$-$C_6$ alkylthio, $C_2$-$C_6$ alkenyloxy, halogenated $C_2$-$C_6$ alkenyloxy, $C_2$-$C_6$ alkynyloxy, halogenated $C_2$-$C_6$ alkynyloxy, $C_1$-$C_6$ alkylcarbonyl, halogenated $C_1$-$C_6$ alkylcarbonyl, $C_1$-$C_6$ alkylsulfinyl, halogenated $C_1$-$C_6$ alkylsulfinyl, $C_1$-$C_6$ alkylsulfonyl, halogenated $C_1$-$C_6$ alkylsulfonyl, $C_1$-$C_6$ alkylcarbonyloxy, $C_1$-$C_6$ alkylcarbonylamino, $C_1$-$C_6$ alkylsulfonyloxy, $C_1$-$C_6$ alkoxycarbonyl, $C_1$-$C_6$ alkoxy $C_1$-$C_6$ alkoxy, $C_1$-$C_6$ alkoxycarbonyl $C_1$-$C_6$ alkyl, $C_1$-$C_6$ alkoxycarbonylamino $C_1$-$C_6$ alkoxycarbonyl $C_1$-$C_6$ alkoxy, aryl, heteroaryl, aryloxy, heteroaryloxy, aralkyloxy, heteroarylalkyloxy, arylamino and heteroarylamine, wherein the aryl, heteroaryl, aryloxy, heteroaryloxy, aralkyloxy, heteroarylalkyloxy, aralkyloxy or heteroarylalkyloxy is aryl, heteroaryl, aryloxy, heteroaryloxy, aralkyloxy, heteroarylalkyloxy, arylamino or heteroarylamine which is each independently unsubstituted or whose H are substituted by 1-4 following groups: halogen, CN, $NO_2$, $C_1$-$C_6$ alkyl, $C_1$-$C_6$ haloalkyl, $C_1$-$C_6$ haloalkoxy, $C_1$-$C_6$ alkoxy, $C_1$-$C_6$ alkoxycarbonyl or $C_1$-$C_6$ alkylsulfonyl;

n is an integer selected from 0 to 5;

Q is a group selected from $Q_1$-$Q$ 14.

More preferred are compounds of formula (I), wherein $R_1$ is selected from the group consisting of hydrogen, halogen, $C_1$-$C_4$ alkyl, $C_3$-$C_6$ cycloalkyl, halogenated $C_1$-$C_4$ alkyl, $C_2$-$C_4$ alkenyl, halogenated $C_2$-$C_4$ alkenyl, $C_2$-$C_4$ alkynyl, halogenated $C_2$-$C_4$ alkynyl, $C_1$-$C_4$ alkoxy and $C_2$-$C_4$ alkenyloxy:

$R_2$ is selected from the group consisting of hydrogen, halogen, nitro, cyano, $C_1$-$C_4$ alkyl, halogenated $C_1$-$C_4$ alkyl, $C_2$-$C_4$ alkenyl, halogenated $C_2$-$C_4$ alkenyl, $C_2$-$C_4$ alkynyl, halogenated $C_2$-$C_4$ alkynyl, $C_1$-$C_4$ alkoxy, $C_1$-$C_4$ alkyl thiol, $C_1$-$C_4$ alkyl SO, $C_1$-$C_4$ alkyl $SO_2$, halogenated $C_1$-$C_4$ alkyl thiol, halogenated $C_1$-$C_4$ alkyl SO, halogenated $C_1$-$C_4$ alkyl $SO_2$, $C_1$-$C_4$ alkylamino, di($C_1$-$C_4$ alkyl) amino and $C_1$-$C_4$ alkylcarbonyl;

$R_3$ is selected from the group consisting of $C_2$-$C_6$ alkenyl, halogenated $C_2$-$C_6$ alkenyl, $C_2$-$C_6$ alkynyl, halogenated $C_2$-$C_6$ alkynyl, $C_3$-$C_6$ cycloalkenyl, arylmethylene and heteroarylmethylene, wherein the arylmethylene or heteroarylmethylene is arylmethylene or heteroarylmethylene which is unsubstituted or whose H is substituted by n $R_4$ groups;

wherein $R_4$ is one or more groups selected from the group consisting of hydrogen, halogen, hydroxyl, sulfhydryl, amino, CN, $NO_2$, $C_1$-$C_4$ alkyl, halogenated $C_1$-$C_4$ alkyl, $C_3$-$C_8$ cycloalkyl, $C_2$-$C_4$ alkenyl, halogenated $C_2$-$C_4$ alkenyl, $C_2$-$C_4$ alkynyl, halogenated $C_2$-$C_4$ alkynyl, $C_1$-$C_4$ alkylamino, di($C_1$-$C_4$ alkyl) amino, halogenated $C_1$-$C_6$ alkylamino, $C_1$-$C_6$ alkoxy, halogenated $C_1$-$C_4$ alkoxy, $C_1$-$C_4$ alkylthio, halogenated $C_1$-$C_4$ alkylthio, $C_2$-$C_4$ alkenyloxy, halogenated $C_2$-$C_4$ alkenyloxy, $C_2$-$C_4$ alkynyloxy, halogenated $C_2$-$C_4$ alkynyloxy, $C_1$-$C_4$ alkylcarbonyl, halogenated $C_1$-$C_4$ alkylcarbonyl, $C_1$-$C_4$ alkylsulfinyl, halogenated $C_1$-$C_4$ alkylsulfinyl, $C_1$-$C_4$ alkylsulfonyl, halogenated $C_1$-$C_4$ alkylsulfonyl, $C_1$-$C_4$alkylcarbonyloxy, $C_1$-$C_4$ alkylcarbonylamino, $C_1$-$C_4$ alkylsulfonyloxy, $C_1$-$C_4$ alkoxycarbonyl, $C_1$-$C_4$ alkoxy $C_1$-$C_4$ alkoxy, $C_1$-$C_4$ alkoxycarbonyl $C_1$-$C_4$ alkyl, $C_1$-$C_4$ alkoxycarbonylamino, $C_1$-$C_4$ alkoxycarbonyl $C_1$-$C_4$ alkoxy, aryl, heteroaryl, aryloxy, heteroaryloxy, aralkyloxy, heteroarylalkyloxy, acylamino and heteroarylamine, wherein the aryl, heteroaryl, aryloxy, heteroaryloxy, aralkyloxy, heteroarylalkyloxy, aralkyloxy or heteroarylalkyloxy is aryl, heteroaryl, aryloxy, heteroaryloxy, aralkyloxy, heteroarylalkyloxy, arylamino or heteroarylamine which is each independently unsubstituted or whose H is substituted by 1-4 following groups: halogen, CN, $NO_2$, $C_1$-$C_4$ alkyl, $C_1$-$C_4$ haloalkyl, $C_1$-$C_4$ haloalkoxy, $C_1$-$C_4$ alkoxy, $C_1$-$C_4$ alkoxycarbonyl or $C_1$-$C_4$ alkylsulfonyl;

n is an integer selected from 0 to 5;

Q is a group selected from $Q_1$-$Q_9$.

Even more preferred are compounds of formula (I), wherein

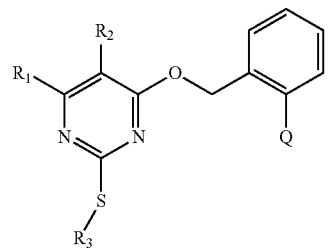

I $R_1$ is hydrogen, chlorine, bromine, methyl, ethyl, n-propyl, isopropyl, cyclopropyl, n-butyl, isobutyl, test-butyl, monofluoromethyl, monochloromethyl, difluoromethyl, trifluoromethyl or trifluoroethyl;

$R_2$ is hydrogen, fluorine, chlorine, bromine, cyano, nitro, methyl, ethyl, n-propyl, isopropyl, n-butyl, isobutyl, methoxy, ethoxy or trifluoroethoxy;

$R_3$ is $CH_2$=$CHCH_2$, $(CH_3)_2C$=$CHCH_2$, $CH_3CH$=$CHCH_2$, $CHCl$=$CHCH_2$, $CH_2$=$CClCH_2$, $CHCl$=$CClCH_2$, $CCl_2$=$CHCH_2$, $CCl_2$=$CClCH_2$, $CF_2$=$CFCH_2$, $CF_2$=$CFCH_2CH_2$, $CH$≡$CCH_2$ or $CH_3C$≡$CCH_2$;

Q is a group selected from $Q_1$-$Q_6$.

And most preferred are compound of formula (I), wherein
R$_1$ is methyl, ethyl, n-propyl, isopropyl, cyclopropyl, difluoromethyl or trifluoromethyl;
R$_2$ is hydrogen, chlorine, nitro, methyl or n-butyl;
R$_3$ is CH$_2$=CHCH$_2$, (CH$_3$)$_2$C=CHCH$_2$, CH$_3$CH=CHCH$_2$, CHCl=CHCH$_2$, CH$_2$=CClCH$_2$, CHCl=CClCH$_2$, CCl$_2$=CHCH$_2$, CCl$_2$=CClCH$_2$, CF$_2$=CFCH$_2$CH$_2$, CH≡CCH$_2$ or CH$_3$C≡CCH$_2$;
Q is a group selected from Q$_1$-Q$_4$.

In the above given definitions of the compounds of formula (I), the used terms generally represent the following substituents:

Halogen: fluorine, chlorine, bromine or iodine.

Alkyl: linear or branched alkyl, such as methyl, ethyl, propyl, isopropyl or tert-butyl.

Halogenated alkyl: linear or branched alkyl in which hydrogen atoms may be partially or completely substituted by halogen, for example, halogenated alkyl such as chloromethyl, dichloromethyl, trichloromethyl, fluoromethyl, difluoromethyl, trifluoromethyl, chlorodifluoromethyl and the like.

Alkoxy: linear or branched alkyl which is connected to the structure via an oxygen atom.

Halogenated alkoxy: linear or branched alkoxy, hydrogen atoms of these alkoxy groups may be partially or completely substituted by halogen, for example, halogenated alkoxy such as chloromethoxy, dichloromethoxy, trichloromethoxy, fluoromethoxy, difluoromethoxy, trifluoromethoxy, chlorofluoromethoxy, trifluoroethoxy.

Alkylthio: linear or branched alkyl which is connected to the structure via a sulfur atom.

Halogenated alkylthio: linear or branched alkylthio, hydrogen atoms of these alkylthio groups may be partially or completely substituted by halogen, for example, halogenated alkylthio such as chloromethylthio, dichloromethylthio, trichloromethylthio, fluoromethylthio, difluoromethylthio, trifluoromethylthio, chlorofluoromethylthio, trifluoroethylthio.

Alkenyl: linear or branched alkenyl, such as ethenyl, 1-propenyl, 2-propenyl, different butenyl, pentenyl and hexenyl isomers. Alkenyl also includes polyenes such as 1,2-propadienyl and 2,4-hexadienyl.

Halogenated alkenyl: linear or branched alkenyl, hydrogen atoms of these alkenyl may be partially or completely substituted by halogen atoms.

Alkynyl: linear or branched alkynyl such as ethynyl, 1-propynyl, 2-propynyl, different butynyl, pentynyl and hexynyl isomers. The alkynyl also includes groups consisting of a plurality of triple bonds, such as 2,5-hexadiynyl.

Halogenated alkynyl: linear or branched alkynyl, hydrogen atoms of these alkynyl may be partially or completely substituted by halogen atoms.

Alkoxyalkyl: alkoxy is connected to the structure via an alkyl group. For example, CH$_3$OCH$_2$—, CH$_3$CH$_2$OCH$_2$—.

Halogenated alkoxyalkyl: hydrogen atoms on alkyl of alkoxyalkyl may be partially or completely substituted by halogen atoms. For example, ClCH$_2$CH$_2$OCH$_2$—.

Alkoxycarbonyl: alkoxy is connected to the structure via a carbonyl group. For example, CH$_3$OCO—, CH$_3$CH$_2$OCO—.

Alkoxycarbonylalkyl: alkoxycarbonyl is attached to the structure via an alkyl group.

Halogenated alkylthioalkyl: halogenated alkylthio is connected to the structure via an alkyl group.

Alkylamino: linear or branched alkyl is connected to the structure via a nitrogen atom.

Alkylaminocarbonyl: such as CH$_3$NHCO—, CH$_3$CH$_2$NHCO—.

Halogenated alkylaminocarbonyl: hydrogen atoms on alkyl of alkylaminocarbonyl may be partially or completely substituted by halogen atoms, such as CF$_3$NHCO—.

Halogenated alkylamino: linear or branched alkylaminoin, hydrogen atoms on these alkyl groups may be partially or completely substituted by halogen atoms.

Alkenyloxy: linear or branched alkenyl is connected to the structure through via an oxygen atom bond.

Halogenated alkenyloxy: linear or branched alkenyloxy, hydrogen atoms of these alkenyloxy groups may be partially or completely substituted by halogen atoms.

Alkynyloxy: linear or branched alkynyl is connected to the structure via an oxygen atom.

Halogenated alkynyloxy: linear or branched alkynyloxy, hydrogen atoms of these alkynyloxy groups may be partially or completely substituted by halogen atoms.

Alkylcarbonyl: alkyl is connected to the structure via carbonyl, such as CH$_3$CO—, CH$_3$CH$_2$O—.

Halogenated alkylcarbonyl: hydrogen atoms on alkyl of alkylcarbonyl may be partially or completely substituted by halogen atoms, such as CF$_3$CO—.

Alkylsulfinyl: linear or branched alkyl is connected to the structure via sulfinyl(—SO—), such as methylsulfinyl.

Halogenated alkylsulfinyl: linear or branched alkylsulfinyl, in which hydrogen atoms on alkyl may be partially or completely substituted by halogen atoms.

Alkylsulfonyl: linear or branched alkyl is connected to the structure via sulfonyl(—SO$_2$—), such as methylsulfonyl.

Halogenated alkylsulfonyl: linear or branched alkylsulfonyl in which hydrogen atoms on alkyl may be partially or completely substituted by halogen atoms.

Phenoxycarbonyl: phenoxy is connected to the structure via carbonyl, such as PhOCO—.

Phenylaminocarbonyl: phenylamino is connected to the structure via carbonyl, such as PhNHCO—.

Phenylalkyl: phenyl is connected to the structure via alkyl, such as benzyl, phenethyl and the like.

Aryl moiety of aryl, aralkyl, aryloxy and aryloxyalkyl includes phenyl and naphthyl.

The heteroaryl in the present invention is a 5-membered ring or a 6-membered ring comprising one or more N, O, S hetero atoms. For example, pyridine, furan, pyrazine, pyridazine, quinoline or benzofuran.

In the present invention, because carbon-carbon double bond or carbon-nitrogen double bond is connected to different substituents, the compound may form stereoisomers (different configurations are represented by Z and E, respectively). The present invention includes both Z-isomers and E: isomers, as well as mixtures thereof in any ratio.

Partial compounds of the general formula (I) in the present invention are illustrated by specific compounds and physical properties thereof listed in table 1-table 4, however, which are not used to limit the present invention.

Some examples of the compounds of formula (I) where

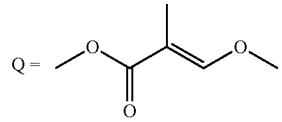

are shown in table 1:
TABLE 1
| Number | R₁ | R₂ | R₃ | Q | Appearance |
|---|---|---|---|---|---|
| 1 | CH₃ | H | 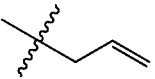 [SMILES: *CC=C] | Q₁ | |
| 2 | CHF₂ | H | 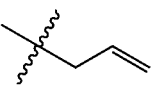 | Q₁ | |
| 3 | CF₃ | H | 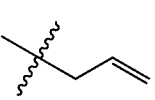 [SMILES: *CC=C] | Q₁ | |
| 4 | C₂H₅ | H |  | Q₁ | |
| 5 | n-C₃H₇ | H |  | Q₁ | |
| 6 | i-C₃H₇ | H | 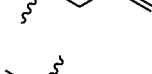 | Q₁ | |
| 7 | 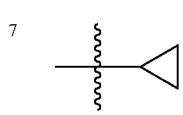 | H | 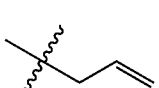 | Q₁ | |
| 8 | CH₃ | Cl | 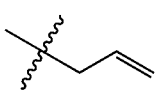 [SMILES: *CC=C] | Q₁ | |
| 9 | CHF₂ | Cl |  | Q₁ | |
| 10 | CF₃ | Cl |  | Q₁ | |
| 11 | C₂H₅ | Cl | 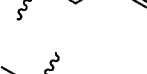 | Q₁ | |
| 12 | n-C₃H₇ | Cl | 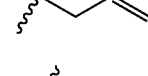 | Q₁ | |
| 13 | i-C₃H₇ | Cl | 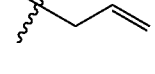 | Q₁ | |
| 14 | 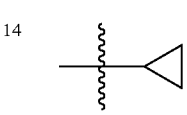 | Cl | 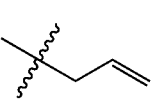 [SMILES: *CC=C] | Q₁ | |
| 15 | CH₃ | CH₃ | 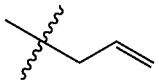 [SMILES: *CC=C] | Q₁ | |

TABLE 1-continued
| Number | R₁ | R₂ | R₃ | Q | Appearance |
|---|---|---|---|---|---|
| 16 | CH₃ | CH₃CH₂CH₂CH₂ | 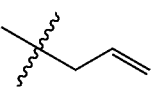 [SMILES: *CC=C] | Q₁ | |
| 17 | CH₃ | H | 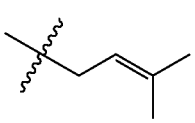 [SMILES: *CC=C(C)C] | Q₁ | |
| 18 | CHF₂ | H | 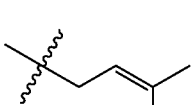 | Q₁ | |
| 19 | CF₃ | H | 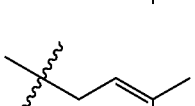 | Q₁ | |
| 20 | C₂H₅ | H | 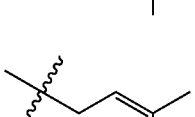 | Q₁ | |
| 21 | n-C₃H₇ | H |  | Q₁ | |
| 22 | i-C₃H₇ | H | 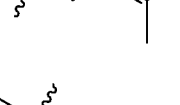 | Q₁ | |
| 23 | 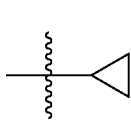 [SMILES: *C1CC1] | H | 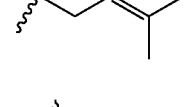 | Q₁ | |
| 24 | CH₃ | Cl | 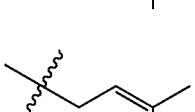 | Q₁ | |
| 25 | CHF₂ | Cl |  | Q₁ | |
| 26 | CF₃ | Cl |  | Q₁ | |
| 27 | C₂H₅ | Cl | 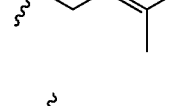 | Q₁ | |

TABLE 1-continued
| Number | R₁ | R₂ | R₃ | Q | Appearance |
|---|---|---|---|---|---|
| 28 | n-C₃H₇ | Cl | 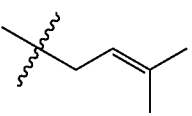 [SMILES: *CC=C(C)C] | Q₁ | |
| 29 | i-C₃H₇ | Cl | 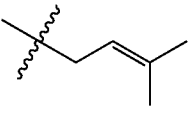 [SMILES: *CC=C(C)C] | Q₁ | |
| 30 | 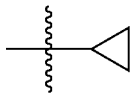 [SMILES: *C1CC1] | Cl | 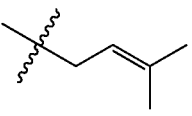 [SMILES: *CC=C(C)C] | Q₁ | |
| 31 | CH₃ | CH₃ | 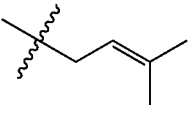 [SMILES: *CC=C(C)C] | Q₁ | |
| 32 | CH₃ | CH₃CH₂CH₂CH₂ | 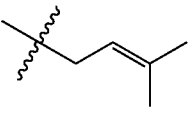 [SMILES: *CC=C(C)C] | Q₁ | |
| 33 | CH₃ | H | 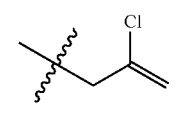 | Q₁ | |
| 34 | CHF₂ | H | 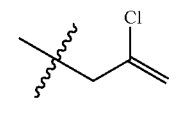 | Q₁ | |
| 35 | CF₃ | H | 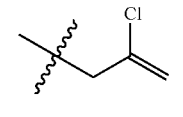 | Q₁ | |
| 36 | C₂H₅ | H | 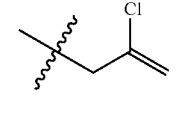 | Q₁ | |
| 37 | n-C₃H₇ | H | 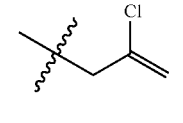 [SMILES: *CC(=C)Cl] | Q₁ | |
| 38 | i-C₃H₇ | H | 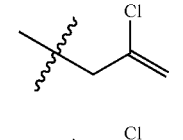 | Q₁ | |
| 39 | 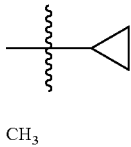 | H | 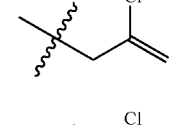 | Q₁ | |
| 40 | CH₃ | Cl | 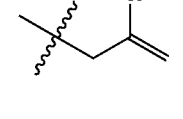 | Q₁ | |

TABLE 1-continued
| Number | R₁ | R₂ | R₃ | Q | Appearance |
|---|---|---|---|---|---|
| 41 | CHF₂ | Cl | 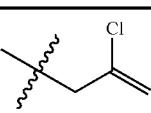 | Q₁ | |
| 42 | CF₃ | Cl | 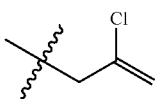 | Q₁ | |
| 43 | C₂H₅ | Cl | 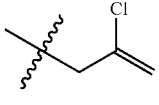 [SMILES: *CC(=C)Cl] | Q₁ | |
| 44 | n-C₃H₇ | Cl | 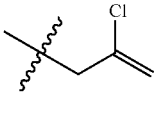 [SMILES: *CC(=C)Cl] | Q₁ | |
| 45 | i-C₃H₇ | Cl | 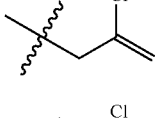 | Q₁ | |
| 46 | 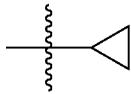 [SMILES: *C1CC1] | Cl | 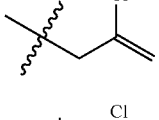 | Q₁ | |
| 47 | CH₃ | CH₃ | 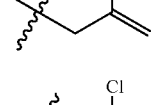 | Q₁ | |
| 48 | CH₃ | CH₃CH₂CH₂CH₂ | 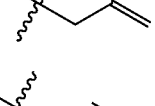 | Q₁ | |
| 49 | CH₃ | H | 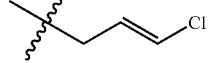 | Q₁ | |
| 50 | CHF₂ | H | 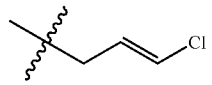 | Q₁ | |
| 51 | CF₃ | H |  | Q₁ | |
| 52 | C₂H₅ | H |  | Q₁ | |
| 53 | n-C₃H₇ | H | 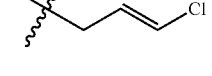 | Q₁ | |
| 54 | i-C₃H₇ | H | 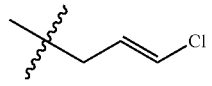 [SMILES: *C/C=C/Cl] | Q₁ | |
| 55 | 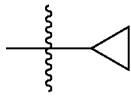 [SMILES: *C1CC1] | H |  | Q₁ | |

TABLE 1-continued

| Number | R₁ | R₂ | R₃ | Q | Appearance |
|---|---|---|---|---|---|
| 56 | CH₃ | Cl | –CH₂–CH=CH–Cl | Q₁ | |
| 57 | CHF₂ | Cl | –CH₂–CH=CH–Cl | Q₁ | |
| 58 | CF₃ | Cl | –CH₂–CH=CH–Cl | Q₁ | |
| 59 | C₂H₅ | Cl | –CH₂–CH=CH–Cl | Q₁ | |
| 60 | n-C₃H₇ | Cl | –CH₂–CH=CH–Cl | Q₁ | |
| 61 | i-C₃H₇ | Cl | –CH₂–CH=CH–Cl | Q₁ | |
| 62 | cyclopropyl | Cl | –CH₂–CH=CH–Cl | Q₁ | |
| 63 | CH₃ | CH₃ | –CH₂–CH=CH–Cl | Q₁ | |
| 64 | CH₃ | CH₃CH₂CH₂CH₂ | –CH₂–CH=CH–Cl | Q₁ | |
| 65 | CH₃ | H | –CH₂–CH=CCl₂ | Q₁ | Yellow oil |
| 66 | CHF₂ | H | –CH₂–CH=CCl₂ | Q₁ | |
| 67 | CF₃ | H | –CH₂–CH=CCl₂ | Q₁ | White solid |
| 68 | C₂H₅ | H | –CH₂–CH=CCl₂ | Q₁ | Light brown oil |
| 69 | n-C₃H₇ | H | –CH₂–CH=CCl₂ | Q₁ | Yellow oil |

TABLE 1-continued
| Number | R₁ | R₂ | R₃ | Q | Appearance |
|---|---|---|---|---|---|
| 70 | i-C₃H₇ | H | 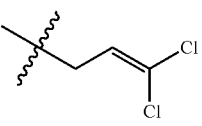 [SMILES: *CC=C(Cl)Cl] | Q₁ | |
| 71 | 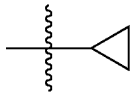 [SMILES: *C1CC1] | H | 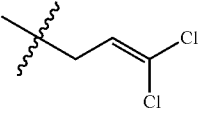 [SMILES: *CC=C(Cl)Cl] | Q₁ | Reddish brown oil |
| 72 | CH₃ | Cl | 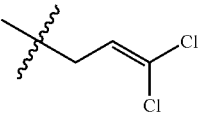 [SMILES: *CC=C(Cl)Cl] | Q₁ | |
| 73 | CHF₂ | Cl | 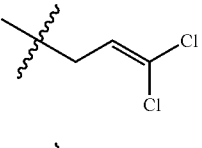 | Q₁ | |
| 74 | CF₃ | Cl | 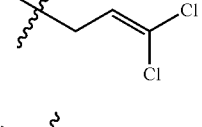 | Q₁ | |
| 75 | C₂H₅ | Cl | 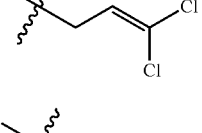 | Q₁ | |
| 76 | n-C₃H₇ | Cl | 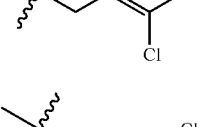 | Q₁ | |
| 77 | i-C₃H₇ | Cl | 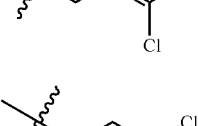 | Q₁ | |
| 78 |  | Cl | 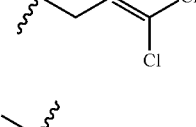 | Q₁ | |
| 79 | CH₃ | CH₃ | 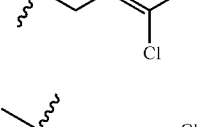 | Q₁ | |
| 80 | CH₃ | CH₃CH₂CH₂CH₂ | 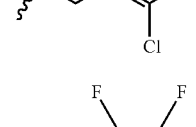 | Q₁ | |
| 81 | CH₃ | H | 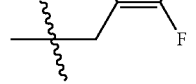 | Q₁ | |

TABLE 1-continued
| Number | R₁ | R₂ | R₃ | Q | Appearance |
|---|---|---|---|---|---|
| 82 | CHF₂ | H | 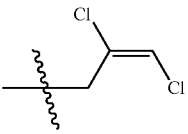 | $Q_1$ | |
| 83 | CF₃ | H | 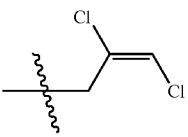 [SMILES: *C/C(Cl)=C\Cl] | $Q_1$ | |
| 84 | C₂H₅ | H | 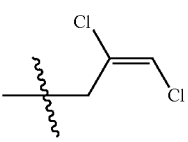 | $Q_1$ | |
| 85 | n-C₃H₇ | H | 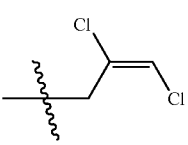 | $Q_1$ | |
| 86 | i-C₃H₇ | H | 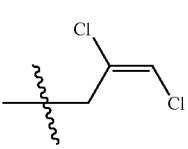 [SMILES: *C/C(Cl)=C\Cl] | $Q_1$ | |
| 87 | 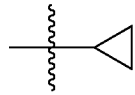 | H | 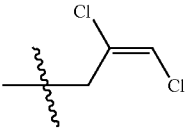 | $Q_1$ | |
| 88 | CH₃ | Cl | 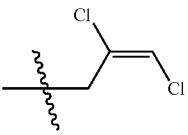 [SMILES: *C/C(Cl)=C\Cl] | $Q_1$ | |
| 89 | CHF₂ | Cl | 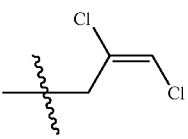 | $Q_1$ | |
| 90 | CF₃ | Cl | 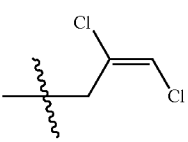 | $Q_1$ | |
| 91 | C₂H₅ | Cl | 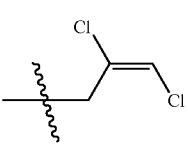 | $Q_1$ | |

TABLE 1-continued
| Number | R₁ | R₂ | R₃ | Q | Appearance |
|---|---|---|---|---|---|
| 92 | n-C₃H₇ | Cl | 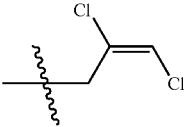 [SMILES: *C/C(Cl)=C\Cl] | Q₁ | |
| 93 | i-C₃H₇ | Cl | 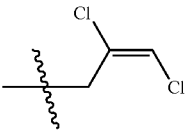 | Q₁ | |
| 94 | 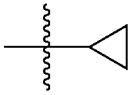 [SMILES: *C1CC1] | Cl | 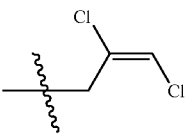 | Q₁ | |
| 95 | CH₃ | CH₃ | 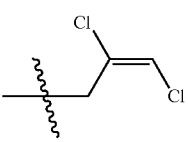 | Q₁ | |
| 96 | CH₃ | CH₃CH₂CH₂CH₂ | 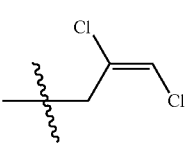 [SMILES: *C/C(Cl)=C\Cl] | Q₁ | |
| 97 | CH₃ | H | 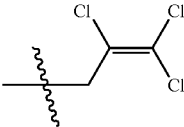 | Q₁ | |
| 98 | CHF₂ | H | 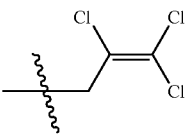 | Q₁ | |
| 99 | CF₃ | H | 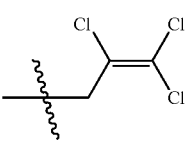 | Q₁ | |
| 100 | C₂H₅ | H | 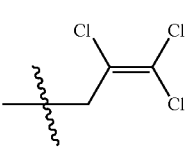 | Q₁ | |
| 101 | n-C₃H₇ | H | 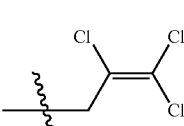 | Q₁ | |
| 102 | i-C₃H₇ | H | 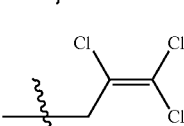 | Q₁ | |

TABLE 1-continued

| Number | R₁ | R₂ | R₃ | Q | Appearance |
|---|---|---|---|---|---|
| 103 | cyclopropyl | H | -CH₂-C(Cl)=CCl₂ | Q₁ | |
| 104 | CH₃ | Cl | -CH₂-C(Cl)=CCl₂ | Q₁ | |
| 105 | CHF₂ | Cl | -CH₂-C(Cl)=CCl₂ | Q₁ | |
| 106 | CF₃ | Cl | -CH₂-C(Cl)=CCl₂ | Q₁ | |
| 107 | C₂H₅ | Cl | -CH₂-C(Cl)=CCl₂ | Q₁ | |
| 108 | n-C₃H₇ | Cl | -CH₂-C(Cl)=CCl₂ | Q₁ | |
| 109 | i-C₃H₇ | Cl | -CH₂-C(Cl)=CCl₂ | Q₁ | |
| 110 | cyclopropyl | Cl | -CH₂-C(Cl)=CCl₂ | Q₁ | |
| 111 | CH₃ | CH₃ | -CH₂-C(Cl)=CCl₂ | Q₁ | |
| 112 | CH₃ | CH₃CH₂CH₂CH₂ | -CH₂-C(Cl)=CCl₂ | Q₁ | |
| 113 | CH₃ | H | -CH₂CH₂CH₂-C(F)=CF | Q₁ | Light yellow oil |

TABLE 1-continued

| Number | R₁ | R₂ | R₃ | Q | Appearance |
|---|---|---|---|---|---|
| 114 | $CHF_2$ | H | CH₂CH₂CH₂C(F)=CF (4,4-difluorobut-3-enyl) | $Q_1$ | Brown oil |
| 115 | $CF_3$ | H | CH₂CH₂CH₂C(F)=CF | $Q_1$ | Light yellow oil |
| 116 | $C_2H_5$ | H | CH₂CH₂CH₂C(F)=CF | $Q_1$ | Light brown oil |
| 117 | $n\text{-}C_3H_7$ | H | CH₂CH₂CH₂C(F)=CF | $Q_1$ | Light brown oil |
| 118 | $i\text{-}C_3H_7$ | H | CH₂CH₂CH₂C(F)=CF | $Q_1$ | Yellow oil |
| 119 | cyclopropyl | H | CH₂CH₂CH₂C(F)=CF | $Q_1$ | Yellow oil |
| 120 | $CH_3$ | Cl | CH₂CH₂CH₂C(F)=CF | $Q_1$ | |
| 121 | $CHF_2$ | Cl | CH₂CH₂CH₂C(F)=CF | $Q_1$ | |
| 122 | $CF_3$ | Cl | CH₂CH₂CH₂C(F)=CF | $Q_1$ | |
| 123 | $C_2H_5$ | Cl | CH₂CH₂CH₂C(F)=CF | $Q_1$ | |
| 124 | $n\text{-}C_3H_7$ | Cl | CH₂CH₂CH₂C(F)=CF | $Q_1$ | |
| 125 | $i\text{-}C_3H_7$ | Cl | CH₂CH₂CH₂C(F)=CF | $Q_1$ | |
| 126 | cyclopropyl | Cl | CH₂CH₂CH₂C(F)=CF | $Q_1$ | |
| 127 | $CH_3$ | $CH_3$ | CH₂CH₂CH₂C(F)=CF | $Q_1$ | |

TABLE 1-continued

| Number | R₁ | R₂ | R₃ | Q | Appearance |
|---|---|---|---|---|---|
| 128 | CH₃ | CH₃CH₂CH₂CH₂ | -CH₂CH₂CH=CF₂ | Q₁ | |
| 129 | CH₃ | H | -CH₂C≡CH (propargyl extended) | Q₁ | |
| 130 | CHF₂ | H | -CH₂C≡CH | Q₁ | |
| 131 | CF₃ | H | -CH₂C≡CH | Q₁ | |
| 132 | C₂H₅ | H | -CH₂C≡CH | Q₁ | |
| 133 | n-C₃H₇ | H | -CH₂C≡CH | Q₁ | |
| 134 | i-C₃H₇ | H | -CH₂C≡CH | Q₁ | |
| 135 | cyclopropyl | H | -CH₂C≡CH | Q₁ | |
| 136 | CH₃ | Cl | -CH₂C≡CH | Q₁ | |
| 137 | CHF₂ | Cl | -CH₂C≡CH | Q₁ | |
| 138 | CF₃ | Cl | -CH₂C≡CH | Q₁ | |
| 139 | C₂H₅ | Cl | -CH₂C≡CH | Q₁ | |
| 140 | n-C₃H₇ | Cl | -CH₂C≡CH | Q₁ | |
| 141 | i-C₃H₇ | Cl | -CH₂C≡CH | Q₁ | |
| 142 | cyclopropyl | Cl | -CH₂C≡CH | Q₁ | |

TABLE 1-continued

| Number | $R_1$ | $R_2$ | $R_3$ | Q | Appearance |
|---|---|---|---|---|---|
| 143 | $CH_3$ | $CH_3$ | propargyl | $Q_1$ | |
| 144 | $CH_3$ | $CH_3CH_2CH_2CH_2$ | propargyl | $Q_1$ | |

Some examples of the compounds of formula (I) where

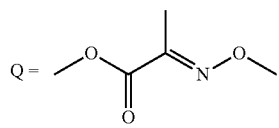

are shown in table

TABLE 2

| Number | $R_1$ | $R_2$ | $R_3$ | Q | Appearance |
|---|---|---|---|---|---|
| 145 | $CH_3$ | H | allyl | $Q_2$ | |
| 146 | $CHF_2$ | H | allyl | $Q_2$ | |
| 147 | $CF_3$ | H | allyl | $Q_2$ | |
| 148 | $C_2H_5$ | H | allyl | $Q_2$ | |
| 149 | n-$C_3H_7$ | H | allyl | $Q_2$ | |
| 150 | i-$C_3H_7$ | H | allyl | $Q_2$ | |
| 151 | cyclopropyl | H | allyl | $Q_2$ | |
| 152 | $CH_3$ | Cl | allyl | $Q_2$ | |
| 153 | $CHF_2$ | Cl | allyl | $Q_2$ | |
| 154 | $CF_3$ | Cl | allyl | $Q_2$ | |

TABLE 2-continued

| Number | R₁ | R₂ | R₃ | Q | Appearance |
|---|---|---|---|---|---|
| 155 | C₂H₅ | Cl | CH₂CH=CH₂ | Q₂ | |
| 156 | n-C₃H₇ | Cl | CH₂CH=CH₂ | Q₂ | |
| 157 | i-C₃H₇ | Cl | CH₂CH=CH₂ | Q₂ | |
| 158 | cyclopropyl | Cl | CH₂CH=CH₂ | Q₂ | |
| 159 | CH₃ | CH₃ | CH₂CH=CH₂ | Q₂ | |
| 160 | CH₃ | CH₃CH₂CH₂CH₂ | CH₂CH=CH₂ | Q₂ | |
| 161 | CH₃ | H | CH₂CH=C(CH₃)₂ | Q₂ | |
| 162 | CHF₂ | H | CH₂CH=C(CH₃)₂ | Q₂ | |
| 163 | CF₃ | H | CH₂CH=C(CH₃)₂ | Q₂ | |
| 164 | C₂H₅ | H | CH₂CH=C(CH₃)₂ | Q₂ | |
| 165 | n-C₃H₇ | H | CH₂CH=C(CH₃)₂ | Q₂ | |
| 166 | i-C₃H₇ | H | CH₂CH=C(CH₃)₂ | Q₂ | |
| 167 | cyclopropyl | H | CH₂CH=C(CH₃)₂ | Q₂ | |

TABLE 2-continued

| Number | $R_1$ | $R_2$ | $R_3$ | Q | Appearance |
|---|---|---|---|---|---|
| 168 | $CH_3$ | Cl | prenyl | $Q_2$ | |
| 169 | $CHF_2$ | Cl | prenyl | $Q_2$ | |
| 170 | $CF_3$ | Cl | prenyl | $Q_2$ | |
| 171 | $C_2H_5$ | Cl | prenyl | $Q_2$ | |
| 172 | n-$C_3H_7$ | Cl | prenyl | $Q_2$ | |
| 173 | i-$C_3H_7$ | Cl | prenyl | $Q_2$ | |
| 174 | cyclopropylmethyl | Cl | prenyl | $Q_2$ | |
| 175 | $CH_3$ | $CH_3$ | prenyl | $Q_2$ | |
| 176 | $CH_3$ | $CH_3CH_2CH_2CH_2$ | prenyl | $Q_2$ | |
| 177 | $CH_3$ | H | 2-chloroallyl | $Q_2$ | |
| 258 | $CHF_2$ | H | 2-chloroallyl | $Q_2$ | |
| 179 | $CF_3$ | H | 2-chloroallyl | $Q_2$ | |
| 180 | $C_2H_5$ | H | 2-chloroallyl | $Q_2$ | |

TABLE 2-continued
| Number | R₁ | R₂ | R₃ | Q | Appearance |
|---|---|---|---|---|---|
| 181 | n-C₃H₇ | H | 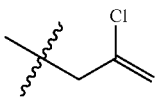 [SMILES: *CC(=C)Cl] | Q₂ | |
| 182 | i-C₃H₇ | H | 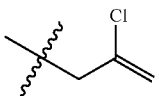 | Q₂ | |
| 183 | 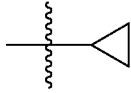 [SMILES: *C1CC1] | H | 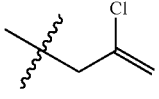 | Q₂ | |
| 184 | CH₃ | Cl | 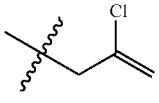 [SMILES: *CC(=C)Cl] | Q₂ | |
| 185 | CHF₂ | Cl | 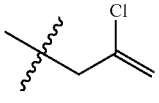 [SMILES: *CC(=C)Cl] | Q₂ | |
| 186 | CF₃ | Cl | 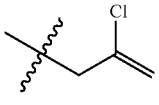 | Q₂ | |
| 187 | C₂H₅ | Cl | 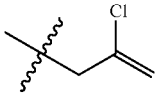 [SMILES: *CC(=C)Cl] | Q₂ | |
| 188 | n-C₃H₇ | Cl | 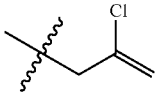 | Q₂ | |
| 189 | i-C₃H₇ | Cl | 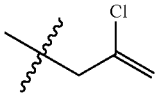 [SMILES: *CC(=C)Cl] | Q₂ | |
| 190 | 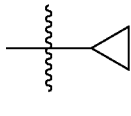 [SMILES: *C1CC1] | Cl | 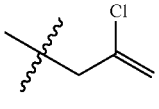 [SMILES: *CC(=C)Cl] | Q₂ | |
| 191 | CH₃ | CH₃ | 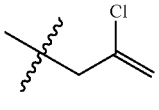 | Q₂ | |
| 192 | CH₃ | CH₃CH₂CH₂CH₂ | 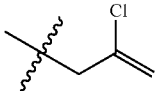 [SMILES: *CC(=C)Cl] | Q₂ | |
| 193 | CH₃ | H | 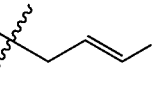 | Q₂ | |
| 194 | CHF₂ | H | 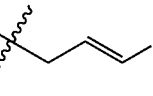 | Q₂ | |

TABLE 2-continued
| Number | R₁ | R₂ | R₃ | Q | Appearance |
|---|---|---|---|---|---|
| 195 | CF₃ | H | 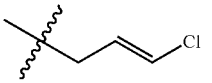 | Q₂ | |
| 196 | C₂H₅ | H | 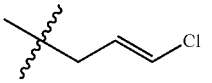 [SMILES: *C/C=C/Cl] | Q₂ | |
| 197 | n-C₃H₇ | H | 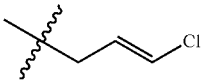 | Q₂ | |
| 198 | i-C₃H₇ | H | 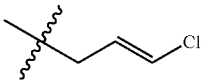 | Q₂ | |
| 199 | 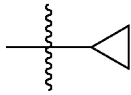 [SMILES: *C1CC1] | H | 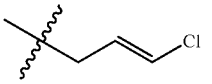 [SMILES: *C/C=C/Cl] | Q₂ | |
| 200 | CH₃ | Cl | 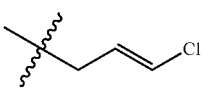 [SMILES: *C/C=C/Cl] | Q₂ | |
| 201 | CHF₂ | Cl | 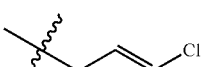 | Q₂ | |
| 202 | CF₃ | Cl | 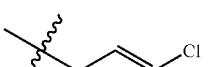 | Q₂ | |
| 203 | C₂H₅ | Cl | 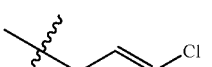 | Q₂ | |
| 204 | n-C₃H₇ | Cl | 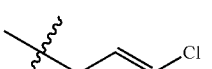 | Q₂ | |
| 205 | i-C₃H₇ | Cl | 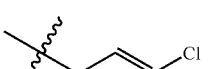 | Q₂ | |
| 206 | 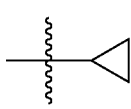 | Cl | 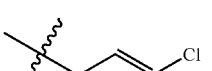 | Q₂ | |
| 207 | CH₃ | CH₃ |  | Q₂ | |
| 208 | CH₃ | CH₃CH₂CH₂CH₂ |  | Q₂ | |
| 209 | CH₃ | H | 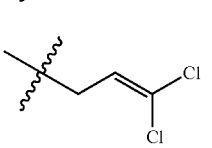 | Q₂ | Yellow oil |

TABLE 2-continued
| Number | R₁ | R₂ | R₃ | Q | Appearance |
|---|---|---|---|---|---|
| 210 | CHF₂ | H | 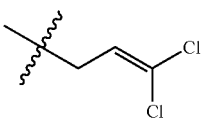 [SMILES: *CC=C(Cl)Cl] | Q₂ | Yellow oil |
| 211 | CF₃ | H | 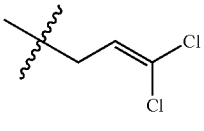 [SMILES: *CC=C(Cl)Cl] | Q₂ | |
| 212 | C₂H₅ | H | 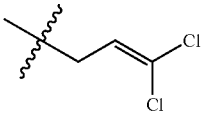 [SMILES: *CC=C(Cl)Cl] | Q₂ | Yellow oil |
| 213 | n-C₃H₇ | H | 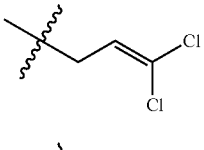 | Q₂ | Yellow oil |
| 214 | i-C₃H₇ | H | 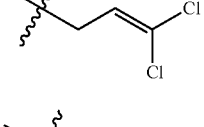 | Q₂ | Yellow oil |
| 215 | 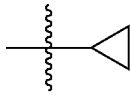 | H | 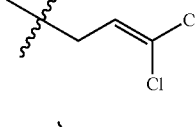 | Q₂ | Yellow oil |
| 216 | CH₃ | Cl | 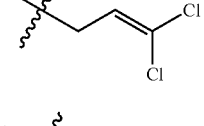 | Q₂ | |
| 217 | CHF₂ | Cl | 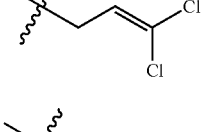 | Q₂ | |
| 218 | CF₃ | Cl | 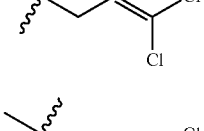 | Q₂ | |
| 219 | C₂H₅ | Cl | 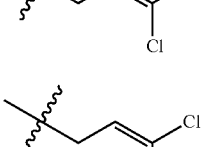 | Q₂ | |
| 220 | n-C₃H₇ | Cl | 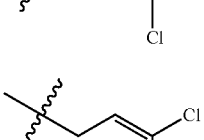 | Q₂ | |
| 221 | i-C₃H₇ | Cl | 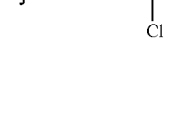 | Q₂ | |

TABLE 2-continued
| Number | R$_1$ | R$_2$ | R$_3$ | Q | Appearance |
|---|---|---|---|---|---|
| 222 | 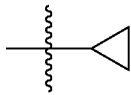 | Cl | 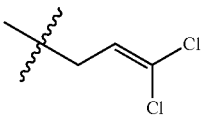 [SMILES: *CC=C(Cl)Cl] | Q$_2$ | |
| 223 | CH$_3$ | CH$_3$ | 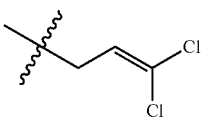 [SMILES: *CC=C(Cl)Cl] | Q$_2$ | |
| 224 | CH$_3$ | CH$_3$CH$_2$CH$_2$CH$_2$ | 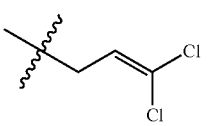 | Q$_2$ | |
| 225 | CH$_3$ | H | 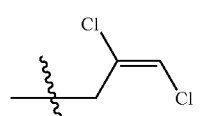 | Q$_2$ | |
| 226 | CHF$_2$ | H | 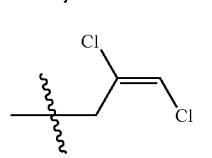 | Q$_2$ | |
| 227 | CF$_3$ | H | 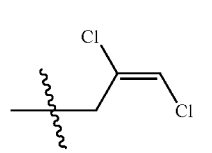 | Q$_2$ | |
| 228 | C$_2$H$_5$ | H | 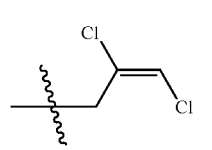 [SMILES: *C/C(Cl)=C\Cl] | Q$_2$ | |
| 229 | n-C$_3$H$_7$ | H | 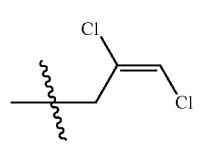 | Q$_2$ | |
| 230 | i-C$_3$H$_7$ | H | 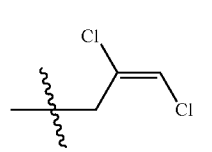 [SMILES: *C/C(Cl)=C\Cl] | Q$_2$ | |
| 231 | 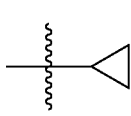 | H | 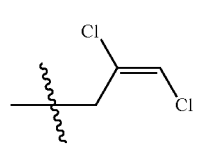 [SMILES: *C/C(Cl)=C\Cl] | Q$_2$ | |
| 232 | CH$_3$ | Cl | 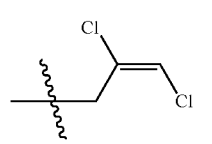 [SMILES: *C/C(Cl)=C\Cl] | Q$_2$ | |

TABLE 2-continued

| Number | R₁ | R₂ | R₃ | Q | Appearance |
|---|---|---|---|---|---|
| 233 | CHF₂ | Cl | CCl=CHCl | Q₂ | |
| 234 | CF₃ | Cl | CCl=CHCl | Q₂ | |
| 235 | C₂H₅ | Cl | CCl=CHCl | Q₂ | |
| 236 | n-C₃H₇ | Cl | CCl=CHCl | Q₂ | |
| 237 | i-C₃H₇ | Cl | CCl=CHCl | Q₂ | |
| 238 | cyclopropyl | Cl | CCl=CHCl | Q₂ | |
| 239 | CH₃ | CH₃ | CCl=CHCl | Q₂ | |
| 240 | CH₃ | CH₃CH₂CH₂CH₂ | CCl=CHCl | Q₂ | |
| 241 | CH₃ | H | CCl=CCl₂ | Q₂ | |
| 242 | CHF₂ | H | CCl=CCl₂ | Q₂ | |
| 243 | CF₃ | H | CCl=CCl₂ | Q₂ | |

TABLE 2-continued
| Number | R₁ | R₂ | R₃ | Q | Appearance |
|---|---|---|---|---|---|
| 244 | C₂H₅ | H | 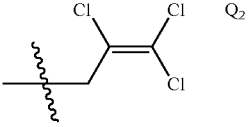 | Q₂ | |
| 245 | n-C₃H₇ | H | 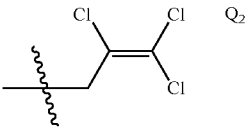 | Q₂ | |
| 246 | i-C₃H₇ | H | 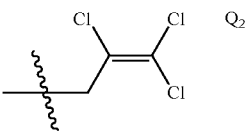 | Q₂ | |
| 247 | 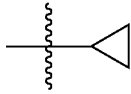 | H | 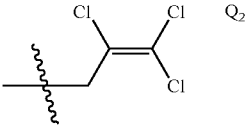 | Q₂ | |
| 248 | CH₃ | Cl | 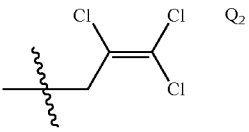 | Q₂ | |
| 249 | CHF₂ | Cl | 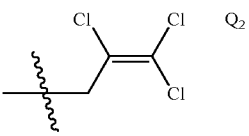 | Q₂ | |
| 250 | CF₃ | Cl | 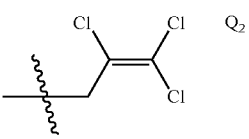 | Q₂ | |
| 251 | C₂H₅ | Cl | 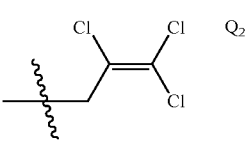 | Q₂ | |
| 252 | n-C₃H₇ | Cl | 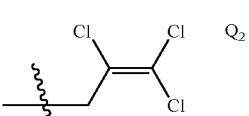 | Q₂ | |
| 253 | i-C₃H₇ | Cl | 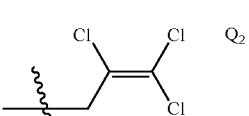 | Q₂ | |

TABLE 2-continued

| Number | R₁ | R₂ | R₃ | Q | Appearance |
|---|---|---|---|---|---|
| 254 | cyclopropyl | Cl | -CH₂-C(Cl)=CCl₂ | Q₂ | |
| 255 | CH₃ | CH₃ | -CH₂-C(Cl)=CCl₂ | Q₂ | |
| 256 | CH₃ | CH₃CH₂CH₂CH₂ | -CH₂-C(Cl)=CCl₂ | Q₂ | |
| 257 | CH₃ | H | -CH₂CH₂CH₂-C(F)=CF₂ | Q₂ | Brown oil |
| 259 | CF₃ | H | -CH₂CH₂CH₂-C(F)=CF₂ | Q₂ | Brown oil |
| 260 | C₂H₅ | H | -CH₂CH₂CH₂-C(F)=CF₂ | Q₂ | Yellow oil |
| 261 | n-C₃H₇ | H | -CH₂CH₂CH₂-C(F)=CF₂ | Q₂ | Yellow oil |
| 262 | i-C₃H₇ | H | -CH₂CH₂CH₂-C(F)=CF₂ | Q₂ | Yellow oil |
| 263 | cyclopropyl | H | -CH₂CH₂CH₂-C(F)=CF₂ | Q₂ | Yellow oil |
| 264 | CH₃ | Cl | -CH₂CH₂CH₂-C(F)=CF₂ | Q₂ | |
| 265 | CHF₂ | Cl | -CH₂CH₂CH₂-C(F)=CF₂ | Q₂ | |
| 266 | CF₃ | Cl | -CH₂CH₂CH₂-C(F)=CF₂ | Q₂ | |
| 267 | C₂H₅ | Cl | -CH₂CH₂CH₂-C(F)=CF₂ | Q₂ | |

TABLE 2-continued

| Number | R₁ | R₂ | R₃ | Q | Appearance |
|---|---|---|---|---|---|
| 268 | n-C₃H₇ | Cl | CH₂CH₂CH=CF₂ | Q₂ | |
| 269 | i-C₃H₇ | Cl | CH₂CH₂CH=CF₂ | Q₂ | |
| 270 | cyclopropyl | Cl | CH₂CH₂CH=CF₂ | Q₂ | |
| 271 | CH₃ | CH₃ | CH₂CH₂CH=CF₂ | Q₂ | |
| 272 | CH₃ | CH₃CH₂CH₂CH₂ | CH₂CH₂CH=CF₂ | Q₂ | |
| 273 | CH₃ | H | CH₂C≡CH | Q₂ | |
| 274 | CHF₂ | H | CH₂C≡CH | Q₂ | |
| 275 | CF₃ | H | CH₂C≡CH | Q₂ | |
| 276 | C₂H₅ | H | CH₂C≡CH | Q₂ | |
| 277 | n-C₃H₇ | H | CH₂C≡CH | Q₂ | |
| 278 | i-C₃H₇ | H | CH₂C≡CH | Q₂ | |
| 279 | cyclopropyl | H | CH₂C≡CH | Q₂ | |
| 280 | CH₃ | Cl | CH₂C≡CH | Q₂ | |
| 281 | CHF₂ | Cl | CH₂C≡CH | Q₂ | |
| 282 | CF₃ | Cl | CH₂C≡CH | Q₂ | |

TABLE 2-continued

| Number | R₁ | R₂ | R₃ | Q | Appearance |
|---|---|---|---|---|---|
| 283 | C₂H₅ | Cl | (CH₂-C≡CH) | Q₂ | |
| 284 | n-C₃H₇ | Cl | (CH₂-C≡CH) | Q₂ | |
| 285 | i-C₃H₇ | Cl | (CH₂-C≡CH) | Q₂ | |
| 286 | cyclopropyl-CH₂ | Cl | (CH₂-C≡CH) | Q₂ | |
| 287 | CH₃ | CH₃ | (CH₂-C≡CH) | Q₂ | |
| 288 | CH₃ | CH₃CH₂CH₂CH₂ | (CH₂-C≡CH) | Q₂ | |

Some examples of the compounds of formula (I) where

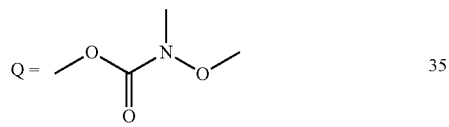

are shown in table 3:

TABLE 3

| Number | R₁ | R₂ | R₃ | Q | Appearance |
|---|---|---|---|---|---|
| 289 | CH₃ | H | (CH₂-CH=CH₂) | Q₃ | |
| 290 | CHF₂ | H | (CH₂-CH=CH₂) | Q₃ | |
| 291 | CF₃ | H | (CH₂-CH=CH₂) | Q₃ | |
| 292 | C₂H₅ | H | (CH₂-CH=CH₂) | Q₃ | |
| 293 | n-C₃H₇ | H | (CH₂-CH=CH₂) | Q₃ | |

TABLE 3-continued
| Number | R₁ | R₂ | R₃ | Q | Appearance |
|---|---|---|---|---|---|
| 294 | i-C₃H₇ | H | 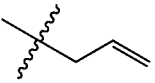 [SMILES: *CC=C] | Q₃ | |
| 295 | 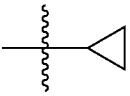 [SMILES: *C1CC1] | H | 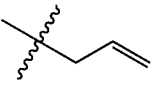 | Q₃ | |
| 296 | CH₃ | Cl | 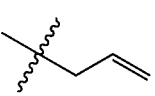 [SMILES: *CC=C] | Q₃ | |
| 297 | CHF₂ | Cl | 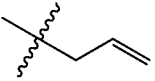 [SMILES: *CC=C] | Q₃ | |
| 298 | CF₃ | Cl | 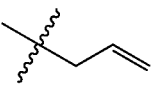 [SMILES: *CC=C] | Q₃ | |
| 299 | C₂H₅ | Cl | 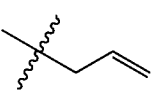 | Q₃ | |
| 300 | n-C₃H₇ | Cl | 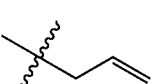 | Q₃ | |
| 301 | i-C₃H₇ | Cl |  | Q₃ | |
| 302 | 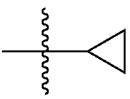 [SMILES: *C1CC1] | Cl | 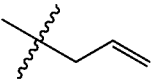 [SMILES: *CC=C] | Q₃ | |
| 303 | CH₃ | CH₃ | 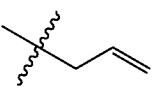 | Q₃ | |
| 304 | CH₃ | CH₃CH₂CH₂CH₂ | 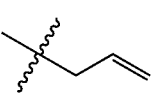 | Q₃ | |
| 305 | CH₃ | H | 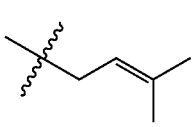 [SMILES: *CC=C(C)C] | Q₃ | |
| 306 | CHF₂ | H | 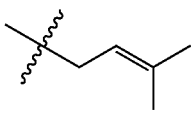 [SMILES: *CC=C(C)C] | Q₃ | |
| 307 | CF₃ | H | 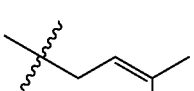 | Q₃ | |

TABLE 3-continued

| Number | R₁ | R₂ | R₃ | Q | Appearance |
|---|---|---|---|---|---|
| 308 | C₂H₅ | H | prenyl | Q₃ | |
| 309 | n-C₃H₇ | H | prenyl | Q₃ | |
| 310 | i-C₃H₇ | H | prenyl | Q₃ | |
| 311 | cyclopropyl | H | prenyl | Q₃ | |
| 312 | CH₃ | Cl | prenyl | Q₃ | |
| 313 | CHF₂ | Cl | prenyl | Q₃ | |
| 314 | CF₃ | Cl | prenyl | Q₃ | |
| 315 | C₂H₅ | Cl | CH₂-C(F)=CF₂ | Q₃ | |
| 316 | n-C₃H₇ | Cl | prenyl | Q₃ | |
| 317 | i-C₃H₇ | Cl | prenyl | Q₃ | |
| 318 | cyclopropyl | Cl | prenyl | Q₃ | |
| 319 | CH₃ | CH₃ | prenyl | Q₃ | |

TABLE 3-continued

| Number | R₁ | R₂ | R₃ | Q | Appearance |
|---|---|---|---|---|---|
| 320 | CH₃ | CH₃CH₂CH₂CH₂ | -CH₂-CH=C(CH₃)₂ | Q₃ | |
| 321 | CH₃ | H | -CH₂-C(Cl)=CH₂ | Q₃ | |
| 322 | CHF₂ | H | -CH₂-C(Cl)=CH₂ | Q₃ | |
| 323 | CF₃ | H | -CH₂-C(Cl)=CH₂ | Q₃ | |
| 324 | C₂H₅ | H | -CH₂-C(Cl)=CH₂ | Q₃ | |
| 325 | n-C₃H₇ | H | -CH₂-C(Cl)=CH₂ | Q₃ | |
| 326 | i-C₃H₇ | H | -CH₂-C(Cl)=CH₂ | Q₃ | |
| 327 | cyclopropyl | H | -CH₂-C(Cl)=CH₂ | Q₃ | |
| 328 | CH₃ | Cl | -CH₂-C(Cl)=CH₂ | Q₃ | |
| 329 | CHF₂ | Cl | -CH₂-C(Cl)=CH₂ | Q₃ | |
| 330 | CF₃ | Cl | -CH₂-C(Cl)=CH₂ | Q₃ | |
| 331 | C₂H₅ | Cl | -CH₂-C(Cl)=CH₂ | Q₃ | |
| 332 | n-C₃H₇ | Cl | -CH₂-C(Cl)=CH₂ | Q₃ | |
| 333 | i-C₃H₇ | Cl | -CH₂-C(Cl)=CH₂ | Q₃ | |

TABLE 3-continued
| Number | R₁ | R₂ | R₃ | Q | Appearance |
|---|---|---|---|---|---|
| 334 | 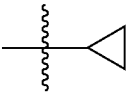 [SMILES: *C1CC1] | Cl | 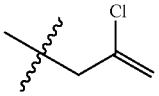 [SMILES: *CC(=C)Cl] | Q₃ | |
| 335 | CH₃ | CH₃ | 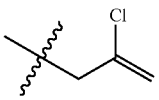 | Q₃ | |
| 336 | CH₃ | CH₃CH₂CH₂CH₂ | 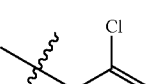 | Q₃ | |
| 337 | CH₃ | H | 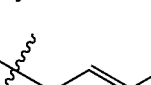 | Q₃ | |
| 338 | CHF₂ | H | 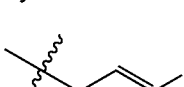 | Q₃ | |
| 339 | CF₃ | H | 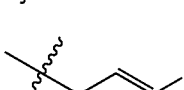 | Q₃ | |
| 340 | C₂H₅ | H | 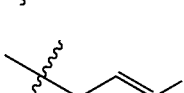 | Q₃ | |
| 341 | n-C₃H₇ | H | 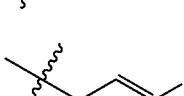 | Q₃ | |
| 342 | i-C₃H₇ | H | 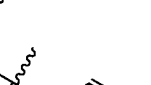 | Q₃ | |
| 343 | 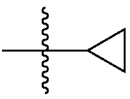 [SMILES: *C1CC1] | H | 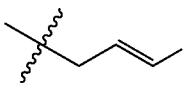 | Q₃ | |
| 344 | CH₃ | Cl | 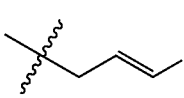 | Q₃ | |
| 345 | CHF₂ | Cl | 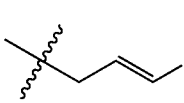 | Q₃ | |
| 346 | CF₃ | Cl | 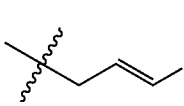 | Q₃ | |
| 347 | C₂H₅ | Cl | 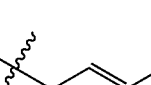 | Q₃ | |
| 348 | n-C₃H₇ | Cl | 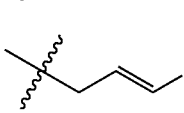 | Q₃ | |

TABLE 3-continued

| Number | R₁ | R₂ | R₃ | Q | Appearance |
|---|---|---|---|---|---|
| 349 | i-C₃H₇ | Cl | CH₂-CH=CH-Cl | Q₃ | |
| 350 | cyclopropyl | Cl | CH₂-CH=CH-Cl | Q₃ | |
| 351 | CH₃ | CH₃ | CH₂-CH=CH-Cl | Q₃ | |
| 352 | CH₃ | CH₃CH₂CH₂CH₂ | CH₂-CH=CH-Cl | Q₃ | |
| 353 | CH₃ | H | CH₂-CH=CCl₂ | Q₃ | Reddish brown oil |
| 354 | CHF₂ | H | CH₂-CH=CCl₂ | Q₃ | Yellow oil |
| 355 | CF₃ | H | CH₂-CH=CCl₂ | Q₃ | |
| 356 | C₂H₅ | H | CH₂-CH=CCl₂ | Q₃ | Yellow oil |
| 357 | n-C₃H₇ | H | CH₂-CH=CCl₂ | Q₃ | Yellow oil |
| 358 | i-C₃H₇ | H | CH₂-CH=CCl₂ | Q₃ | Yellow oil |
| 359 | cyclopropyl | H | CH₂-CH=CCl₂ | Q₃ | Yellow oil |
| 360 | CH₃ | Cl | CH₂-CH=CCl₂ | Q₃ | |
| 361 | CHF₂ | Cl | CH₂-CH=CCl₂ | Q₃ | |

TABLE 3-continued
| Number | R₁ | R₂ | R₃ | Q | Appearance |
|---|---|---|---|---|---|
| 362 | CF₃ | Cl | 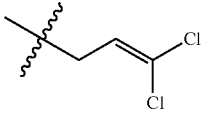 | Q₃ | |
| 363 | C₂H₅ | Cl | 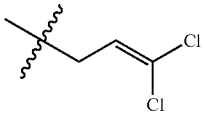 [SMILES: *CC=C(Cl)Cl] | Q₃ | |
| 364 | n-C₃H₇ | Cl | 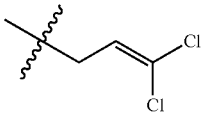 | Q₃ | |
| 365 | i-C₃H₇ | Cl | 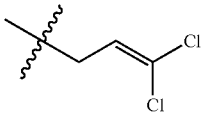 | Q₃ | |
| 366 | 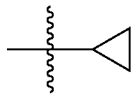 [SMILES: *C1CC1] | Cl | 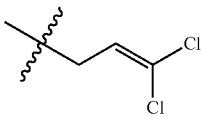 [SMILES: *CC=C(Cl)Cl] | Q₃ | |
| 367 | CH₃ | CH₃ | 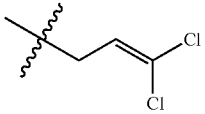 | Q₃ | |
| 368 | CH₃ | CH₃CH₂CH₂CH₂ | 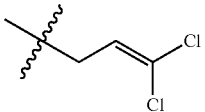 | Q₃ | |
| 369 | CH₃ | H | 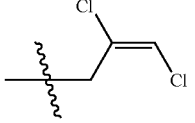 [SMILES: *C/C(Cl)=C\Cl] | Q₃ | |
| 370 | CHF₂ | H | 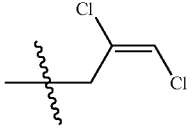 [SMILES: *C/C(Cl)=C\Cl] | Q₃ | |
| 371 | CF₃ | H | 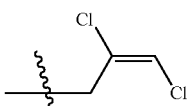 | Q₃ | |
| 372 | C₂H₅ | H | 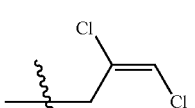 | Q₃ | |

TABLE 3-continued
| Number | R₁ | R₂ | R₃ | Q | Appearance |
|---|---|---|---|---|---|
| 373 | n-C₃H₇ | H | 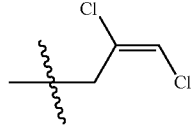 [SMILES: *C/C(Cl)=C\Cl] | Q₃ | |
| 374 | i-C₃H₇ | H | 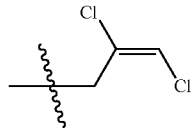 | Q₃ | |
| 375 | 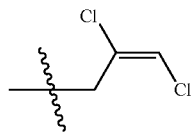 [SMILES: *C/C(Cl)=C\Cl] | H | 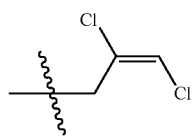 [SMILES: *C/C(Cl)=C\Cl] | Q₃ | |
| 376 | CH₃ | Cl | 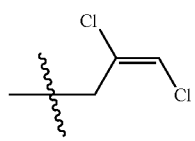 [SMILES: *C/C(Cl)=C\Cl] | Q₃ | |
| 377 | CHF₂ | Cl | | Q₃ | |
| 378 | CF₃ | Cl | 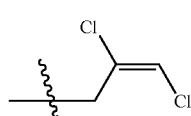 | Q₃ | |
| 379 | C₂H₅ | Cl | 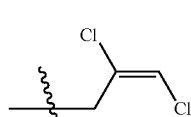 | Q₃ | |
| 380 | n-C₃H₇ | Cl | 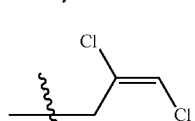 | Q₃ | |
| 381 | i-C₃H₇ | Cl | 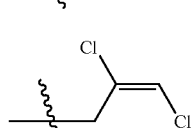 | Q₃ | |
| 382 | 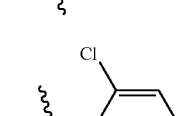 | Cl | 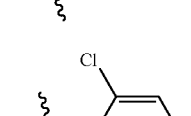 | Q₃ | |
| 383 | CH₃ | CH₃ | | Q₃ | |

TABLE 3-continued
| Number | R$_1$ | R$_2$ | R$_3$ | Q | Appearance |
|---|---|---|---|---|---|
| 384 | CH$_3$ | CH$_3$CH$_2$CH$_2$CH$_2$ | 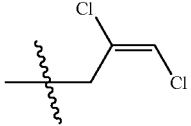 [SMILES: *C/C(Cl)=C\Cl] | Q$_3$ | |
| 385 | CH$_3$ | H | 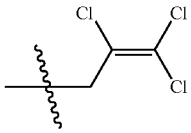 [SMILES: *CC(Cl)=C(Cl)Cl] | Q$_3$ | |
| 386 | CHF$_2$ | H | 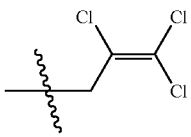 [SMILES: *CC(Cl)=C(Cl)Cl] | Q$_3$ | |
| 387 | CF$_3$ | H | 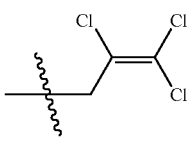 [SMILES: *CC(Cl)=C(Cl)Cl] | Q$_3$ | |
| 388 | C$_2$H$_5$ | H | 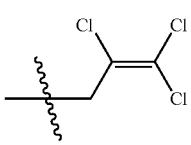 [SMILES: *CC(Cl)=C(Cl)Cl] | Q$_3$ | |
| 389 | n-C$_3$H$_7$ | H | 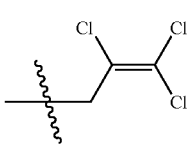 [SMILES: *CC(Cl)=C(Cl)Cl] | Q$_3$ | |
| 390 | i-C$_3$H$_7$ | H | 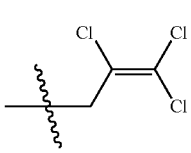 [SMILES: *CC(Cl)=C(Cl)Cl] | Q$_3$ | |
| 391 | 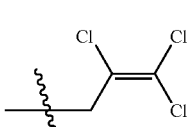 | H | 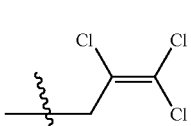 | Q$_3$ | |
| 392 | CH$_3$ | Cl | 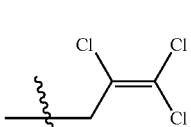 | Q$_3$ | |
| 393 | CHF$_2$ | Cl | | Q$_3$ | |

TABLE 3-continued
| Number | R₁ | R₂ | R₃ | Q | Appearance |
|---|---|---|---|---|---|
| 394 | CF₃ | Cl | 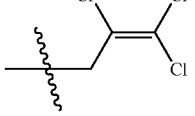 | Q₃ | |
| 395 | C₂H₅ | Cl | 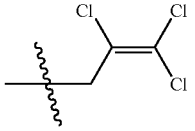 [SMILES: *CC(Cl)=C(Cl)Cl] | Q₃ | |
| 396 | n-C₃H₇ | Cl | 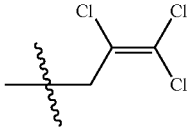 [SMILES: *CC(Cl)=C(Cl)Cl] | Q₃ | |
| 397 | i-C₃H₇ | Cl | 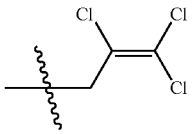 [SMILES: *CC(Cl)=C(Cl)Cl] | Q₃ | |
| 398 | 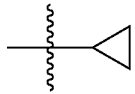 [SMILES: *C1CC1] | Cl | 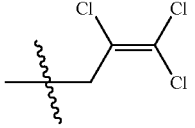 [SMILES: *CC(Cl)=C(Cl)Cl] | Q₃ | |
| 399 | CH₃ | CH₃ | 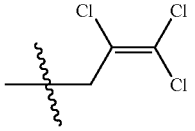 [SMILES: *CC(Cl)=C(Cl)Cl] | Q₃ | |
| 400 | CH₃ | CH₃CH₂CH₂CH₂ | 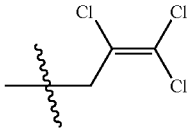 [SMILES: *CC(Cl)=C(Cl)Cl] | Q₃ | |
| 401 | CH₃ | H | 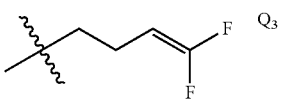 | Q₃ | Yellow viscous liquid |
| 402 | CHF₂ | H | 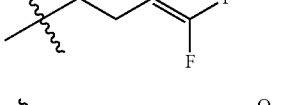 | Q₃ | Light yellow oil |
| 403 | CF₃ | H | 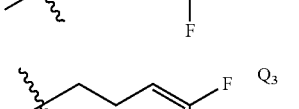 | Q₃ | Yellow oil |
| 404 | C₂H₅ | H | 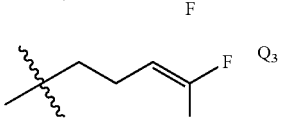 | Q₃ | Light brown oil |
| 405 | n-C₃H₇ | H |  | Q₃ | Light brown oil |

TABLE 3-continued

| Number | R₁ | R₂ | R₃ | Q | Appearance |
|---|---|---|---|---|---|
| 406 | i-C₃H₇ | H | CH₂CH₂CH=CF₂ | Q₃ | Light brown oil |
| 407 | cyclopropyl | H | CH₂CH₂CH=CF₂ | Q₃ | Yellow oil |
| 408 | CH₃ | Cl | CH₂CH₂CH=CF₂ | Q₃ | |
| 409 | CHF₂ | Cl | CH₂CH₂CH=CF₂ | Q₃ | |
| 410 | CF₃ | Cl | CH₂CH₂CH=CF₂ | Q₃ | |
| 411 | C₂H₅ | Cl | CH₂CH₂CH=CF₂ | Q₃ | |
| 412 | n-C₃H₇ | Cl | CH₂CH₂CH=CF₂ | Q₃ | |
| 413 | i-C₃H₇ | Cl | CH₂CH₂CH=CF₂ | Q₃ | |
| 414 | cyclopropyl | Cl | CH₂CH₂CH=CF₂ | Q₃ | |
| 415 | CH₃ | CH₃ | CH₂CH₂CH=CF₂ | Q₃ | |
| 416 | CH₃ | CH₃CH₂CH₂CH₂ | CH₂CH₂CH=CF₂ | Q₃ | |
| 417 | CH₃ | H | CH₂C≡CH | Q₃ | |
| 418 | CHF₂ | H | CH₂C≡CH | Q₃ | |
| 419 | CF₃ | H | CH₂C≡CH | Q₃ | |

TABLE 3-continued
| Number | R₁ | R₂ | R₃ | Q | Appearance |
|---|---|---|---|---|---|
| 420 | C₂H₅ | H | 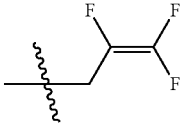 | Q₃ | |
| 421 | n-C₃H₇ | H | 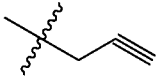 [SMILES: *CC#C] | Q₃ | |
| 422 | i-C₃H₇ | H | 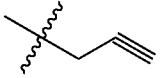 [SMILES: *CC#C] | Q₃ | |
| 423 | 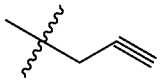 [SMILES: *CC#C] | H | 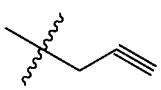 [SMILES: *CC#C] | Q₃ | |
| 424 | CH₃ | Cl | 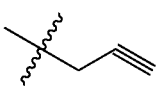 [SMILES: *CC#C] | Q₃ | |
| 425 | CHF₂ | Cl | 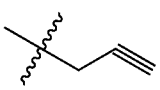 [SMILES: *CC#C] | Q₃ | |
| 426 | CF₃ | Cl | 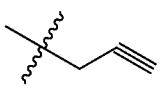 [SMILES: *CC#C] | Q₃ | |
| 427 | C₂H₅ | Cl | 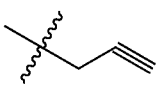 [SMILES: *CC#C] | Q₃ | |
| 428 | n-C₃H₇ | Cl | 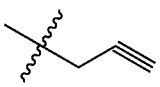 [SMILES: *CC#C] | Q₃ | |
| 429 | i-C₃H₇ | Cl | 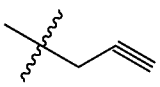 [SMILES: *CC#C] | Q₃ | |
| 430 | 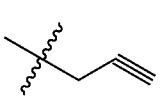 [SMILES: *CC#C] | Cl | 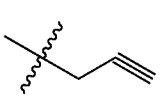 [SMILES: *CC#C] | Q₃ | |
| 431 | CH₃ | CH₃ | | Q₃ | |
| 432 | CH₃ | CH₃CH₂CH₂CH₂ | | Q₃ | |

Some examples of the compounds of formula (I) where
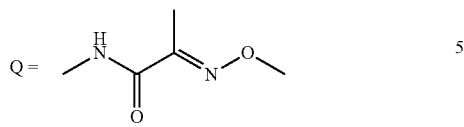
are shown in table 4:
TABLE 4
| Number | R$_1$ | R$_2$ | R$_3$ | Q | Appearance |
|---|---|---|---|---|---|
| 433 | CH$_3$ | H | | Q$_4$ | |
| 434 | CHF$_2$ | H | | Q$_4$ | |
| 435 | CF$_3$ | H | | Q$_4$ | |
| 436 | C$_2$H$_5$ | H | | Q$_4$ | |
| 437 | n-C$_3$H$_7$ | H | | Q$_4$ | |
| 438 | i-C$_3$H$_7$ | H | | Q$_4$ | |
| 439 | cyclopropyl | H | | Q$_4$ | |
| 440 | CH$_3$ | Cl | | Q$_4$ | |
| 441 | CHF$_2$ | Cl | | Q$_4$ | |
| 442 | CF$_3$ | Cl | | Q$_4$ | |
| 443 | C$_2$H$_5$ | Cl | | Q$_4$ | |
| 444 | n-C$_3$H$_7$ | Cl | | Q$_4$ | |
| 445 | i-C$_3$H$_7$ | Cl | | Q$_4$ | |

TABLE 4-continued
| Number | R₁ | R₂ | R₃ | Q | Appearance |
|---|---|---|---|---|---|
| 446 | 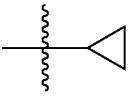 | Cl | 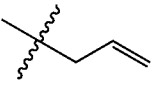 [SMILES: *CC=C] | Q₄ | |
| 447 | CH₃ | CH₃ | 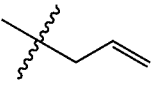 | Q₄ | |
| 448 | CH₃ | CH₃CH₂CH₂CH₂ | 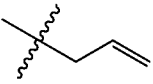 | Q₄ | |
| 449 | CH₃ | H | 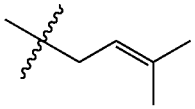 [SMILES: *CC=C(C)C] | Q₄ | |
| 450 | CHF₂ | H | 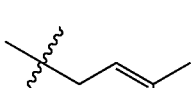 | Q₄ | |
| 451 | CF₃ | H |  | Q₄ | |
| 452 | C₂H₅ | H | 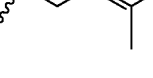 | Q₄ | |
| 453 | n-C₃H₇ | H | 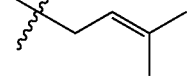 | Q₄ | |
| 454 | i-C₃H₇ | H |  | Q₄ | |
| 455 | 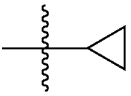 [SMILES: *C1CC1] | H | 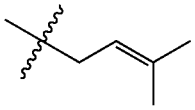 | Q₄ | |
| 456 | CH₃ | Cl | 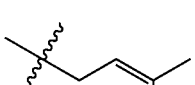 | Q₄ | |
| 457 | CHF₂ | Cl |  | Q₄ | |
| 458 | CF₃ | Cl |  | Q₄ | |

TABLE 4-continued
| Number | R₁ | R₂ | R₃ | Q | Appearance |
|---|---|---|---|---|---|
| 459 | C₂H₅ | Cl | 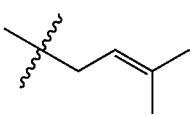 [SMILES: *CC=C(C)C] | Q₄ | |
| 460 | n-C₃H₇ | Cl | 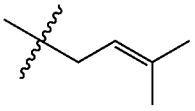 [SMILES: *CC=C(C)C] | Q₄ | |
| 461 | i-C₃H₇ | Cl | 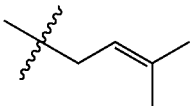 [SMILES: *CC=C(C)C] | Q₄ | |
| 462 | 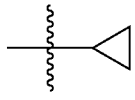 [SMILES: *C1CC1] | Cl | 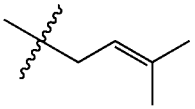 | Q₄ | |
| 463 | CH₃ | CH₃ | 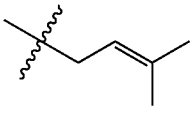 [SMILES: *CC=C(C)C] | Q₄ | |
| 464 | CH₃ | CH₃CH₂CH₂CH₂ | 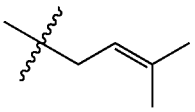 | Q₄ | |
| 465 | CH₃ | H | 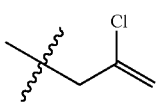 | Q₄ | |
| 466 | CHF₂ | H | 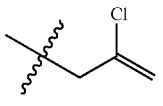 [SMILES: *CC(=C)Cl] | Q₄ | |
| 467 | CF₃ | H | 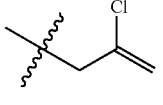 [SMILES: *CC(=C)Cl] | Q₄ | |
| 468 | C₂H₅ | H | 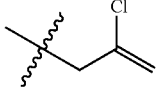 | Q₄ | |
| 469 | n-C₃H₇ | H | 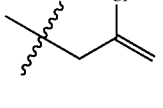 | Q₄ | |
| 470 | i-C₃H₇ | H | 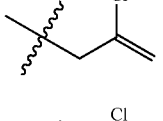 | Q₄ | |
| 471 | 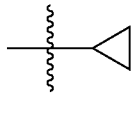 [SMILES: *C1CC1] | H | 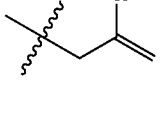 | Q₄ | |

TABLE 4-continued

| Number | R₁ | R₂ | R₃ | Q | Appearance |
|---|---|---|---|---|---|
| 472 | CH₃ | Cl | 2-chloroallyl | Q₄ | |
| 473 | CHF₂ | Cl | 2-chloroallyl | Q₄ | |
| 474 | CF₃ | Cl | 2-chloroallyl | Q₄ | |
| 475 | C₂H₅ | Cl | 2-chloroallyl | Q₄ | |
| 476 | n-C₃H₇ | Cl | 2-chloroallyl | Q₄ | |
| 477 | i-C₃H₇ | Cl | 2-chloroallyl | Q₄ | |
| 478 | cyclopropyl | Cl | 2-chloroallyl | Q₄ | |
| 479 | CH₃ | CH₃ | 2-chloroallyl | Q₄ | |
| 480 | CH₃ | CH₃CH₂CH₂CH₂ | 2-chloroallyl | Q₄ | |
| 481 | CH₃ | H | 4-chloro-3-butenyl | Q₄ | |
| 482 | CHF₂ | H | 4-chloro-3-butenyl | Q₄ | |
| 483 | CF₃ | H | 4-chloro-3-butenyl | Q₄ | |
| 484 | C₂H₅ | H | 4-chloro-3-butenyl | Q₄ | |
| 485 | n-C₃H₇ | H | 4-chloro-3-butenyl | Q₄ | |

TABLE 4-continued
| Number | R₁ | R₂ | R₃ | Q |
|---|---|---|---|---|
| 486 | i-C₃H₇ | H | 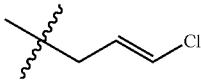 | Q₄ |
| 487 | 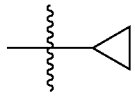 [SMILES: *C1CC1] | H | 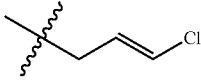 [SMILES: *C/C=C/Cl] | Q₄ |
| 488 | CH₃ | Cl | 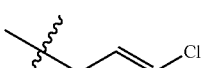 | Q₄ |
| 489 | CHF₂ | Cl | 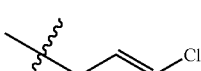 | Q₄ |
| 490 | CF₃ | Cl | 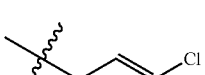 | Q₄ |
| 491 | C₂H₅ | Cl |  | Q₄ |
| 492 | n-C₃H₇ | Cl |  | Q₄ |
| 493 | i-C₃H₇ | Cl |  | Q₄ |
| 494 | 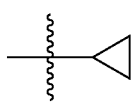 [SMILES: *C1CC1] | Cl | 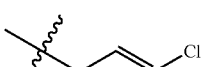 | Q₄ |
| 495 | CH₃ | CH₃ | 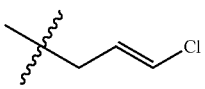 | Q₄ |
| 496 | CH₃ | CH₃CH₂CH₂CH₂ | 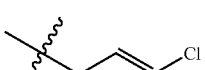 | Q₄ |
| 497 | CH₃ | H |  | Q₄ |
| 498 | CHF₂ | H |  | Q₄ |
| 499 | CF₃ | H | 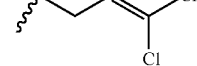 | Q₄ |

TABLE 4-continued

| Number | R₁ | R₂ | R₃ | Q | Appearance |
|---|---|---|---|---|---|
| 500 | C₂H₅ | H | -CH₂-CH=CCl₂ | Q₄ | |
| 501 | n-C₃H₇ | H | -CH₂-CH=CCl₂ | Q₄ | |
| 502 | i-C₃H₇ | H | -CH₂-CH=CCl₂ | Q₄ | |
| 503 | cyclopropyl | H | -CH₂-CH=CCl₂ | Q₄ | |
| 504 | CH₃ | Cl | -CH₂-CH=CCl₂ | Q₄ | |
| 505 | CHF₂ | Cl | -CH₂-CH=CCl₂ | Q₄ | |
| 506 | CF₃ | Cl | -CH₂-CH=CCl₂ | Q₄ | |
| 507 | C₂H₅ | Cl | -CH₂-CH=CCl₂ | Q₄ | |
| 508 | n-C₃H₇ | Cl | -CH₂-CH=CCl₂ | Q₄ | |
| 509 | i-C₃H₇ | Cl | -CH₂-CH=CCl₂ | Q₄ | |
| 510 | cyclopropyl | Cl | -CH₂-CH=CCl₂ | Q₄ | |
| 511 | CH₃ | CH₃ | -CH₂-CH=CCl₂ | Q₄ | |

TABLE 4-continued
| Number | R₁ | R₂ | R₃ | Q | Appearance |
|--------|-----|-----|-----|-----|------------|
| 512 | CH₃ | CH₃CH₂CH₂CH₂ | 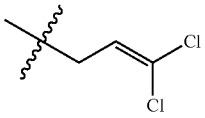 [SMILES: *CC=C(Cl)Cl] | Q₄ | |
| 513 | CH₃ | H | 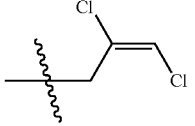 [SMILES: *C/C(Cl)=C\Cl] | Q₄ | |
| 514 | CHF₂ | H | 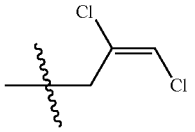 [SMILES: *C/C(Cl)=C\Cl] | Q₄ | |
| 515 | CF₃ | H | 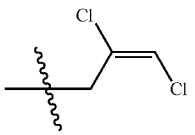 | Q₄ | |
| 516 | C₂H₅ | H | 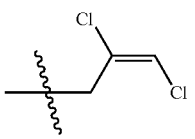 [SMILES: *C/C(Cl)=C\Cl] | Q₄ | |
| 517 | n-C₃H₇ | H | 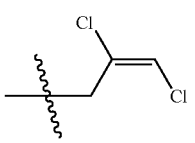 [SMILES: *C/C(Cl)=C\Cl] | Q₄ | |
| 518 | i-C₃H₇ | H | 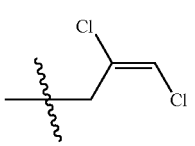 | Q₄ | |
| 519 | 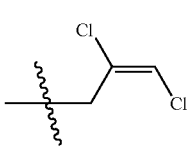 | H | 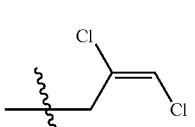 | Q₄ | |
| 520 | CH₃ | Cl | 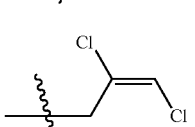 | Q₄ | |
| 521 | CHF₂ | Cl | 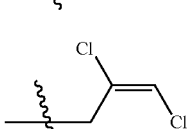 | Q₄ | |
| 522 | CF₃ | Cl | | Q₄ | |

TABLE 4-continued
| Number | R₁ | R₂ | R₃ | Q | Appearance |
|---|---|---|---|---|---|
| 523 | C₂H₅ | Cl | 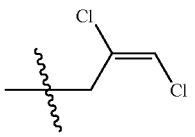 [SMILES: *C/C(Cl)=C\Cl] | Q₄ | |
| 524 | n-C₃H₇ | Cl | 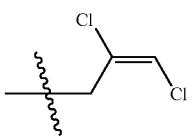 [SMILES: *C/C(Cl)=C\Cl] | Q₄ | |
| 525 | i-C₃H₇ | Cl | 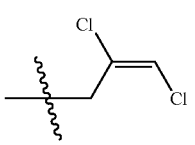 | Q₄ | |
| 526 | 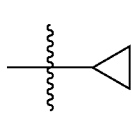 [SMILES: *C1CC1] | Cl | 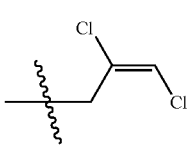 [SMILES: *C/C(Cl)=C\Cl] | Q₄ | |
| 527 | CH₃ | CH₃ | 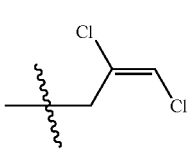 [SMILES: *C/C(Cl)=C\Cl] | Q₄ | |
| 528 | CH₃ | CH₃CH₂CH₂CH₂ | 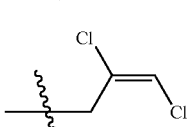 | Q₄ | |
| 529 | CH₃ | H | 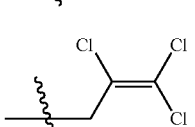 | Q₄ | |
| 530 | CHF₂ | H | 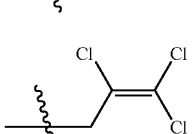 | Q₄ | |
| 531 | CF₃ | H | 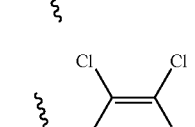 | Q₄ | |
| 532 | C₂H₅ | H | 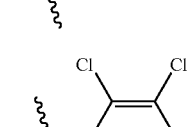 | Q₄ | |
| 533 | n-C₃H₇ | H | 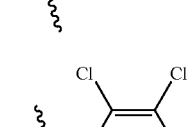 | Q₄ | |

TABLE 4-continued
| Number | R₁ | R₂ | R₃ | Q | Appearance |
|---|---|---|---|---|---|
| 534 | i-C₃H₇ | H | 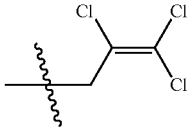 [SMILES: *CC(Cl)=C(Cl)Cl] | Q₄ | |
| 535 | 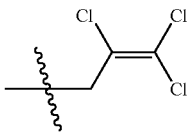 [SMILES: *CC(Cl)=C(Cl)Cl] | H | 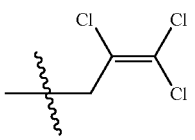 | Q₄ | |
| 536 | CH₃ | Cl | 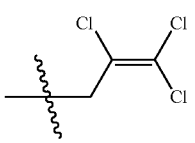 [SMILES: *CC(Cl)=C(Cl)Cl] | Q₄ | |
| 537 | CHF₂ | Cl | 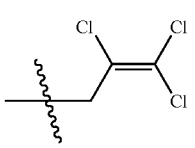 [SMILES: *CC(Cl)=C(Cl)Cl] | Q₄ | |
| 538 | CF₃ | Cl | 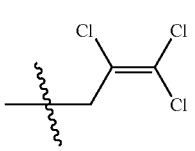 [SMILES: *CC(Cl)=C(Cl)Cl] | Q₄ | |
| 539 | C₂H₅ | Cl | 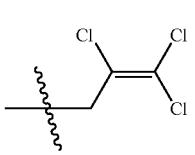 | Q₄ | |
| 540 | n-C₃H₇ | Cl | 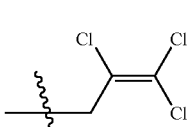 | Q₄ | |
| 541 | i-C₃H₇ | Cl | 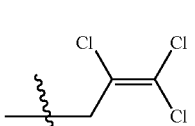 | Q₄ | |
| 542 | 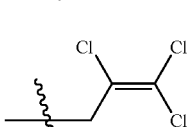 | Cl | | Q₄ | |
| 543 | CH₃ | CH₃ | | Q₄ | |

TABLE 4-continued
| Number | R₁ | R₂ | R₃ | Q | Appearance |
|---|---|---|---|---|---|
| 544 | CH₃ | CH₃CH₂CH₂CH₂ | 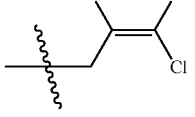 | Q₄ | |
| 545 | | | | | |
| 546 | CH₃ | H | 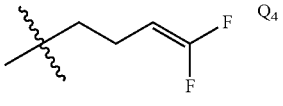 | Q₄ | |
| 547 | CHF₂ | H | 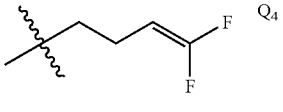 | Q₄ | |
| 548 | CF₃ | H | 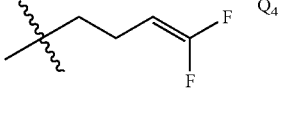 | Q₄ | |
| 549 | C₂H₅ | H | 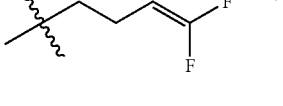 | Q₄ | Yellow oil |
| 550 | n-C₃H₇ | H | 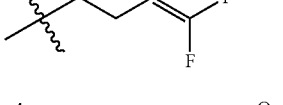 | Q₄ | |
| 551 | i-C₃H₇ | H | 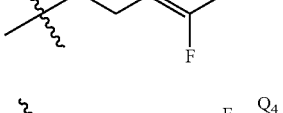 | Q₄ | |
| 552 | 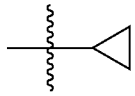 | H | 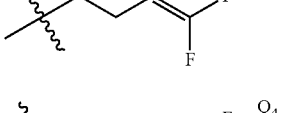 | Q₄ | |
| 553 | CH₃ | Cl | 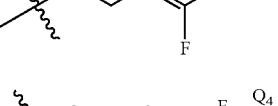 | Q₄ | |
| 554 | CHF₂ | Cl | 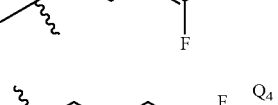 | Q₄ | |
| 555 | CF₃ | Cl | 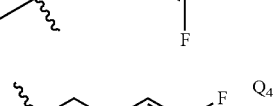 | Q₄ | |
| 556 | C₂H₅ | Cl | 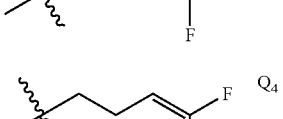 | Q₄ | |
| 557 | n-C₃H₇ | Cl | 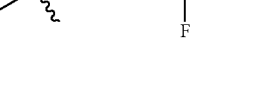 | Q₄ | |

TABLE 4-continued

| Number | R₁ | R₂ | R₃ | Q | Appearance |
|---|---|---|---|---|---|
| 558 | i-C₃H₇ | Cl | CH₂CH₂CH=CF₂ | Q₄ | |
| 559 | cyclopropyl | Cl | CH₂CH₂CH=CF₂ | Q₄ | |
| 560 | CH₃ | CH₃ | CH₂CH₂CH=CF₂ | Q₄ | |
| 561 | CH₃ | CH₃CH₂CH₂CH₂ | CH₂CH₂CH=CF₂ | Q₄ | |
| 562 | CH₃ | H | CH₂C≡CH | Q₄ | |
| 563 | CHF₂ | H | CH₂C≡CH | Q₄ | |
| 564 | CF₃ | H | CH₂C≡CH | Q₄ | |
| 565 | C₂H₅ | H | CH₂C≡CH | Q₄ | |
| 566 | n-C₃H₇ | H | CH₂C≡CH | Q₄ | |
| 567 | i-C₃H₇ | H | CH₂C≡CH | Q₄ | |
| 568 | cyclopropyl | H | CH₂C≡CH | Q₄ | |
| 569 | CH₃ | Cl | CH₂C≡CH | Q₄ | |
| 570 | CHF₂ | Cl | CH₂C≡CH | Q₄ | |
| 571 | CH₃ | Cl | CH₂C≡CH | Q₄ | |
| 572 | C₂H₅ | Cl | CH₂C≡CH | Q₄ | |

TABLE 4-continued

| Number | $R_1$ | $R_2$ | $R_3$ | Q | Appearance |
|---|---|---|---|---|---|
| 573 | n-$C_3H_7$ | Cl | ⸺CH$_2$CH$_2$C≡CH | $Q_4$ | |
| 574 | i-$C_3H_7$ | Cl | ⸺CH$_2$CH$_2$C≡CH | $Q_4$ | |
| 575 | cyclopropyl | Cl | ⸺CH$_2$CH$_2$C≡CH | $Q_4$ | |
| 576 | $CH_3$ | $CH_3$ | ⸺CH$_2$CH$_2$C≡CH | $Q_4$ | |
| 449 | $CH_3$ | $CH_3CH_2CH_2CH_2$ | ⸺CH$_2$CH$_2$C≡CH | $Q_4$ | |

Specifically, preferred compounds of formula (I) are as follows:

Compounds 1, 2, 3, 9, 10, 16, 19, 34, 35, 36, 49, 50, 51, 55, 65, 67, 68, 69, 71, 113, 114, 115, 116, 117, 118, 119, 120, 127, 128, 131, 145, 146, 147, 163, 177, 178, 179, 180, 191, 193, 194, 195, 199, 209, 210, 211, 212, 213, 214, 215, 257, 258, 259, 260, 261, 262, 263, 271, 272, 337, 338, 339, 353, 354, 356, 357, 358, 359, 372, 373, 401, 402, 403, 404, 405, 406, 407, 549.

The present invention also provides a preparation method of the compounds of formula (I), which can be prepared as follows:

In the cases of the compound of formula (I) wherein Q is selected from any one of $Q_1$, $Q_2$, $Q_3$, $Q_6$-$Q_{13}$, the method is carried out as follows: a hydroxyl-containing pyrimidine compound of formula (III) and benzyl halide of formula (IV) are reacted in the presence of an alkaline material and an organic solvent at a temperature ranging from 20 to 100° C. for 0.5 to 20 hours, and then subjected to separation and purification to obtain the corresponding substituted pyrimidine thioether compound of formula (I);

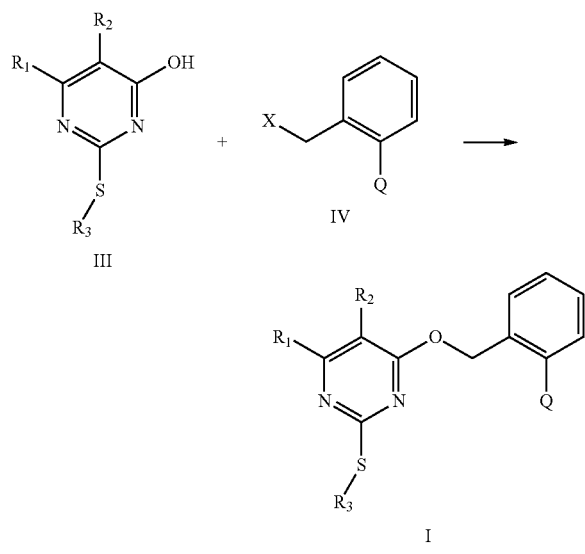

In formula (III) or formula (IV), $R_1$, $R_2$, $R_3$ and Q have the same definitions with that of formula (I), X is a leaving group selected between chlorine and bromine;

In the above method, the molar ratio of the compound of formula (III) to the compound of formula (IV) is ranging from 1:1 to 1:1.1;

The reaction is carried out in a suitable organic solvent, and the suitable organic solvent may be selected from, for example, tetrahydrofuran, acetonitrile, xylene, benzene, DMF, DMSO, acetone, butanone or methyl tert-butyl ether and the like.

The suitable alkaline material is selected from potassium hydroxide, sodium hydroxide, sodium carbonate, potassium carbonate, sodium hydrogencarbonate, triethylamine, pyridine, sodium methoxide, sodium ethoxide, sodium hydride, potassium t-butoxide or sodium t-butoxide and the like.

The reaction temperature may be between room temperature and the boiling point of the solvent, usually between 20° C. and 100° C.

The reaction time is from 30 minutes to 20 hours, usually from 1 to 12 hours.

The separation and purification is carried out as follows: the reaction mixture is poured into a saturated aqueous solution of sodium chloride, and extracted with ethyl acetate for several times, dried, and then evaporated, and then the object product is obtained through purifying by column chromatography with an eluent consisting of petroleum ether and ethyl acetate in a ratio ranging from 1000:1 to 1000:500.

In the cases of the Q in the compound of formula (I) is selected from $Q_4$, $Q_5$ or $Q_{14}$, the preparation method is carried out as follows: the compound of formula (I) in which Q is respectively $Q_2$, $Q_3$ or $Q_{13}$ is further reacted with a methylamine aqueous solution to obtain the compound of formula (I) in which Q is $Q_4$, $Q_5$ or $Q_{14}$, respectively: wherein the mass concentration of the methylamine aqueous solution is between 20% and 60%; the molar ratio of the compound of formula (I) in which Q is $Q_2$, $Q_3$ or $Q_{13}$ to methylamine in the methylamine aqueous solution is ranging from 1:5 to 1:10.

The intermediates of formula (III) can be obtained by condensing the intermediate (II) with halogenated alkene or halogenated alkyne or benzyl halide according to known methods, and the intermediate (II) can be purchased or obtained by known methods.

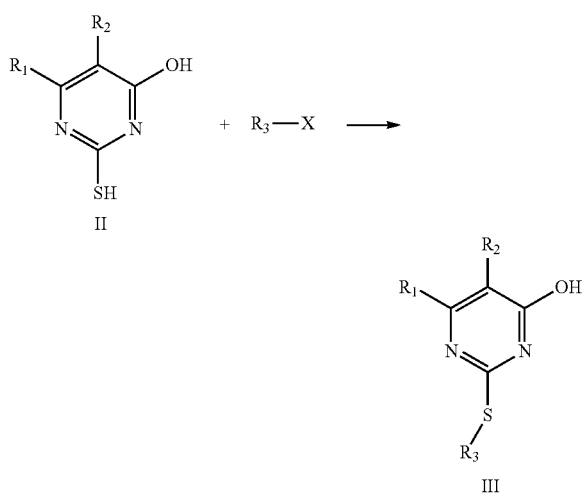

The compounds of formula (IV) can be prepared by known methods, and details can refer to patents U.S. Pat. Nos. 4,723,034, 5,554,578, etc.

Although both the compounds of the general formula (I) in the present invention and some disclosed compounds in prior art belong to methoxy acrylate compounds, their structural properties remain significantly different. And these structural differences lead the compounds of the present invention to have better insecticidal, acaricidal and bactericidal activity.

The following examples of diseases are only used for illustrating the present invention, rather than limiting it.

The compounds of the general formula (I) exhibit high insecticidal and acaricidal activity against adults, larvae and eggs of harmful mites and insects in the agriculture, civil use and animal technology fields. Meanwhile, the compounds also exhibit good bactericidal activity.

Therefore, another object of the present invention relates to application of the compounds of formula (I) as an insecticide and/or a bactericide in agriculture or other fields. Especially, the compounds of formula (I) are active against the following important varieties: Tetranychidae (*Tetranychus urticae*, Tilia *Tetranychus urticae*, *Tetranychus cinnabarinus*, *Carpinus* tetranychidae, *Panonychus ulmi* Koch, *Panonychus citri* McGregor, etc.). Eriophyidae (hazel Phytoptidae, Eriophyes vitis, Eriophyes pyri Pagenstecher, etc.), Tarsonemidae (primrose Steneotarsonemus furcatus, etc.). At the same time, partial compounds of the present invention have good bactericidal activity, and may be used for preventing rice sheath blight disease, rice blast, tomato late blight, cucumber downy mildew, gray mold of cucumber, powdery mildew of cucumber, wheat powdery mildew, wheat gray mold, anthracnose, gibberellic disease, soybean rust, etc.

Meanwhile, the compounds of formula (I) have low toxicity against many beneficial insects and mites, mammals, fishes and birds, and no toxicity against plants.

Due to their positive properties, the above compounds can be beneficially used for protecting important crops, livestocks and stud stocks in agriculture and horticulture, as well as protecting humans from harmful mites and insects in the environments where humans often go.

In order to obtain ideal effects, the use amount of the compound varies depending on various factors. For example, used compound, pre-protected crop, type of harmful organisms, infection degree, climate condition, application method and adopted dosage form.

Sufficient prevention can be provided by the compound dosage ranging from 10 grains to 5 kilograms per hectare.

Another object of the present invention relates to a method of preventing harmful insects and/or phytopathogenic fungi from important crops and/or livestocks and stud stocks in agriculture and horticulture and/or environments where humans often go. Especially, the use amount of the compound works best within the range from 10 grams to 5 kilograms per hectare.

For practical application in agriculture, it is usually beneficial to use a composition containing one or more compounds of formula (I).

Therefore, another object of the present invention relates to an insecticidal and/or bactericidal composition containing one or more compounds of formula I as active component. The composition contains one or more substituted pyrimidine thioether compounds of formula (I) and agriculturally acceptable carriers, wherein the mass fraction of the substituted pyrimidine thioether compounds is ranging from 1% to 90%.

The composition is prepared by known methods, the agriculturally acceptable carriers include: surfactant, solvent medium and/or diluent, etc. For example, optionally in the presence of a surfactant, a solvent medium and/or diluent are used to dissolve or dilute the active substance.

Suitable diluents comprise solid diluents and liquid diluents, and the solid diluent or carrier is, for example, silicon dioxide, kaolin and bentonite, dolomite, dolomite, calcium carbonate, magnesium oxide, chalk, clay, synthetic silicate, magnesium-magnesium soil, sepiolite, sulfate and the like.

In addition to water, suitable liquid diluent is, for example, aromatic organic solvent (mixture of xylem, or alkylbenzene, chlorobenzene and the like), paraffin (petroleum fraction), alcohol (methanol, propyl alcohol, butanol, propylene glycol, ethylene glycol, glycerol, octanol)), ester (ethyl acetate, isobutyl acetate and the like), ketone (cyclohexanone, acetone, acetophenone, isophorone, ethyl nonpolar ketone and the like)), amide (N, N-dimethylformamide, methyl pyrrolidone and the like).

Suitable surfactant is sodium, calcium, triethyl amine or triethanolamine salt of alkyl sulfonates, alkylaryl sulfonates, polyoxyethylene phenol, polyoxyethylene ester of sorbitol, lignosulfonate and the like.

The composition may also contain one or more special additives for specific purpose, for example, adhesives such as arabic gum, polyvinyl alcohol, polyvinylpyrrolidone and the like.

The concentration of the active ingredient (that is, the compound of formula (I)) in the above composition may vary within a wide range depending on the active ingredient, its use purpose, environmental conditions and the type of preparation applied. Generally, the concentration of the active ingredient is ranging from 1 to 90%, preferably from 5 to 50%.

If it is necessary, other active ingredients that are compatible with the compound of the general formula (I) may be added to the composition, such as other acaricides/pesticides, fungicides, plant growth regulators, antibiotics, herbicides and fertilizers.

The advantages of the present invention are: it is the first time that the substituted pyrimidine thioether compounds of formula (I) are discovered and prepared, and the compounds exhibit high insecticidal activity against adult, larvae and eggs of harmful mites and insects in the fields of agriculture, civil use and animal technology. Meanwhile, the compounds exhibit pretty good bactericidal activity. For certain applications, for example, in agriculture, one or more other fungicides, insecticides, acaricides, herbicides, plant growth regulators or fertilizers, etc. may be added to the bactericidal, insecticidal and acaricidal compositions of the present invention, which may create additional advantages and effects.

What should be understood is that various changes and modifications may be made within the scope of the claims of the present invention.

SPECIFIC EMBODIMENTS

The present invention is further illustrated below with reference to specific embodiments, but the present invention is not limited to these specific embodiments. Those skilled in the art should recognize that the present invention encompasses all alternatives, modifications and equivalents that may be included within the scope of the claims.

Example 1

Synthesis of Compound 81

(1) Synthesis of Intermediate 3a

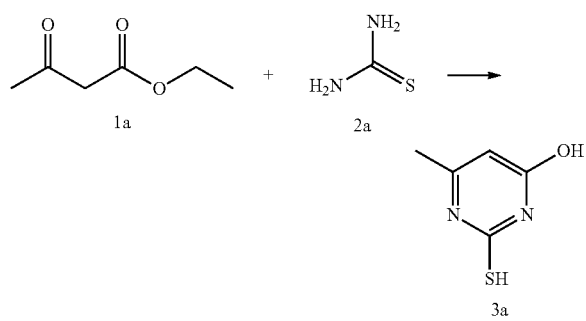

To a solution of 18.24 g (0.24 mol) of thiourea in 150 mL of methanol, a solution of 26.4 g (0.48 mol) of sodium methoxide in methanol was slowly added dropwise with stirring at room temperature, and stirring was continued at room temperature for 2 h. Then, 26 g (0.2 mol) of intermediate, ethyl acetoacetate, was added dropwise to the above solution, and the reaction was stirred at reflux for 6-8 h. After the reaction was detected by TLC, the solvent was evaporated under reduced pressure, the resulting mixture was adjusted to pH 5-6 with hydrochloric acid to precipitate a solid, and then was filtered to a white solid, and after drying, 27 g of the white solid was obtained. The yield was 95%.

(2) Synthesis of Intermediate 5a

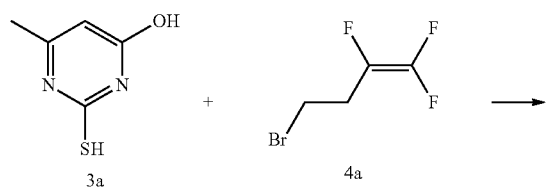

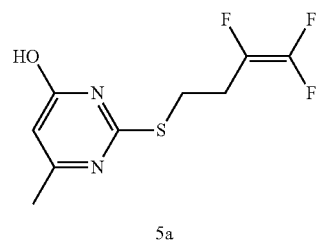

1.42 g (0.01 mol) of 3a was dissolved in 15 mL of N,N-dimethylformamide, and 1.51 g of potassium carbonate was added thereto, and the mixture was stirred for 0.5 h and then of 1.9 g of 4a was added dropwise thereto, and then the temperature was raised to 60° C., and the reaction was stirred for 4 hours. After the reaction was detected by TLC, the solvent was evaporated under reduced pressure, and water was added, and pH was adjusted to 5-6 with hydrochloric acid to precipitate a solid, which was filtered to give a white solid, and after drying, 2.3 g of the white solid was obtained. The yield was 92%.

(3) Synthesis of Compound 81

1.25 g (0.005 mol) of 5a was dissolved in 10 ml of N,N-dimethylformamide, and 0.83 g of potassium carbonate was added thereto, and the mixture was stirred for 0.5 h, and 1.26 g of 6a was added in portions, then, the mixture was heated to 80° C., and stirred for 8 hours. After the reaction was detected by TLC, the reaction solution was poured into 50 ml of saturated brine, and extracted with three portions of ethyl acetate (100 ml) and dried. After desolation, it was purified by column chromatography eluting with petroleum ether: ethyl acetate 1000:1~1400 to yield 1.95 g of oily product.

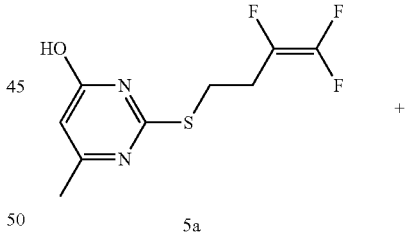

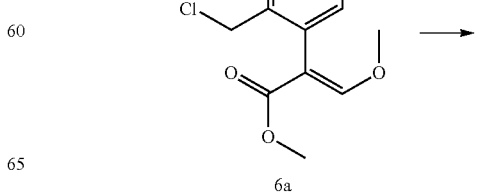

-continued

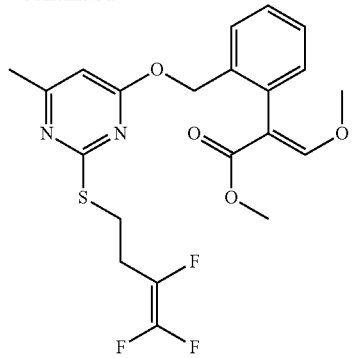

Example 2

Synthesis of the Compound 258

(1) Synthesis of Intermediate 3c 1.78 g (0.01 mol) of 1c was dissolved in 15 ml of N,N-dimethylformamide, and 1.51 g of potassium carbonate was added thereto, and the mixture was stirred for 0.5 h. and 1.2 g of 2c was added dropwise thereto, then, the temperature was raised to 60° C., and the reaction was stirred for 4 hours. After the reaction was detected by TLC, the solvent was evaporated under reduced pressure, and water was added, and pH was adjusted to 5-6 with hydrochloric acid to precipitate a solid, which was filtered to give a white solid, and after drying, 2.2 g of the white solid was obtained. The yield was 86.9%.

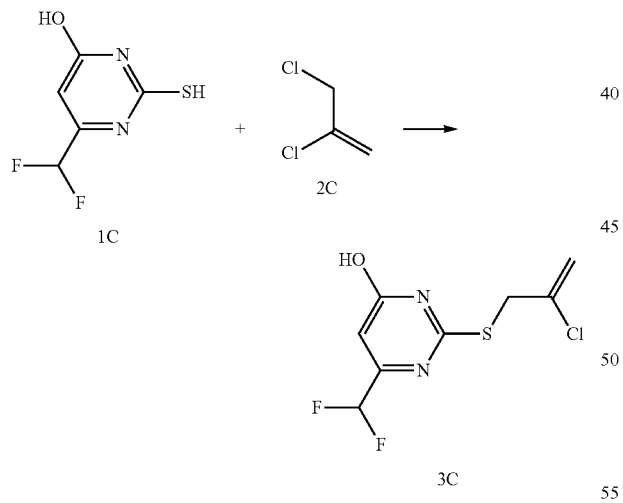

(2) Synthesis of Compound 258

1.3 g (0.005 mol) of 3c was dissolved in 10 ml of N,N-dimethylfomamide, and 0.83 g of potassium carbonate was added thereto, and the mixture was stirred for 0.5 and 1:45 g of 2b was added in portions, then, the mixture was heated to 80° C., and stirred for 8 hours. After the reaction was detected by TLC, the reaction solution was poured into 50 ml of saturated brine, and extracted with three portions of ethyl acetate (100 ml) and dried. After desolvation, it was purified by column chromatography eluting with petroleum ether: ethyl acetate 1000:1-300 to yield 1.86 g of oily product.

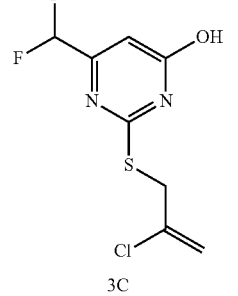

3C

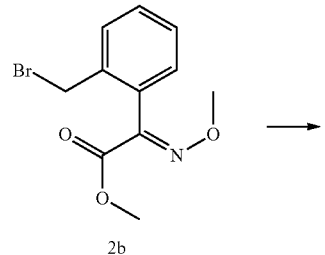

2b

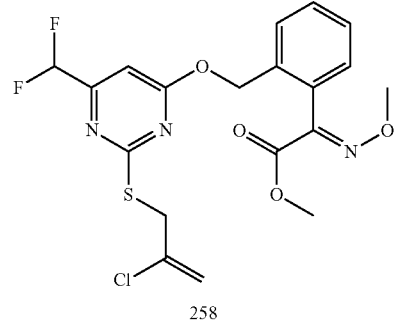

258

Example 3

Synthesis of the Compound 315

1.35 g (0.005 mol) of 1 b was dissolved in 10 ml of N,N-dimethylformamide, and 0.83 g of potassium carbonate was added thereto, and the mixture was stirred for 0.5 and 1:45 g of 2b was added in portions, then, the mixture was heated to 80° C., and stirred for 8 hours. After the reaction was detected by TLC, the reaction solution was poured into 50 ml of saturated brine, and extracted with three portions of ethyl acetate (100 ml) and dried. After desolvation, it was purified by column chromatography eluting with petroleum ether: ethyl acetate 1000:1~300 to yield 1.92 g of oily product.

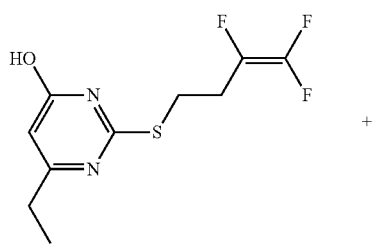

1b

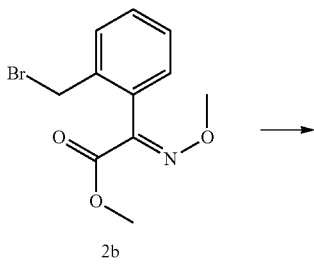

2b

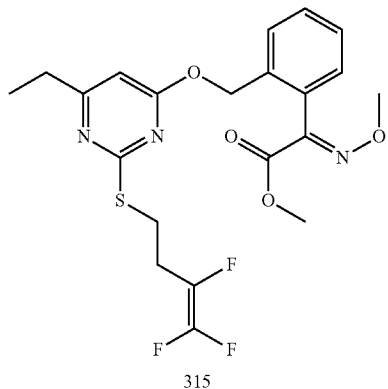

315

Example 4

Synthesis of the Compound 420

1.0 g (0.002 mol) of 1 b was dissolved in 30 ml of ethanol, and 0.85 g of a 40% aqueous solution of methylamine was added thereto, then the mixture was heated to reflux temperature and reacted, the reaction was stirred for 8 hours. After the reaction was detected by TLC and desolvation, it was purified by column chromatography eluting with petroleum ether: ethyl acetate 1000:1~300 to yield 0.86 g of oily product.

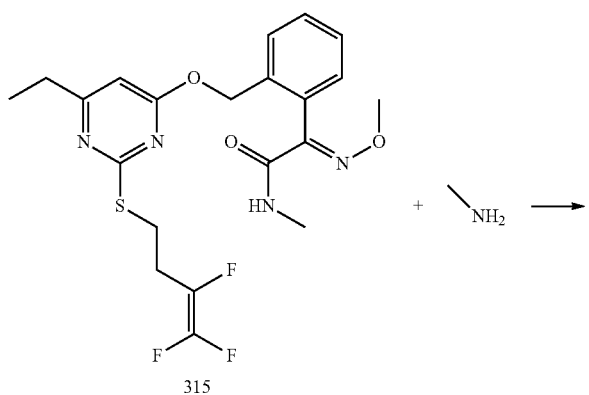

315

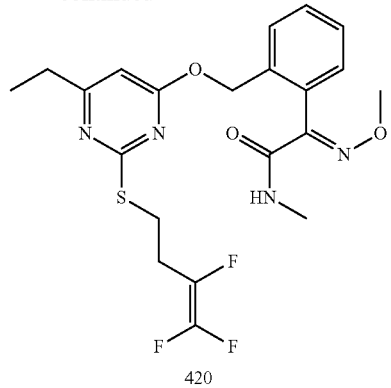

420

The other compounds of the present invention can be prepared with reference to the examples above, and here is no more pleonasm.

Nuclear magnetic data of partial compounds:

Compound 1 $^1$HNMR (400 MHz, DMSO) δ (ppm): 2.31 (s, 3H, CH$_3$), 3.61 (s, 3H, CH$_3$), 3.77-3.78 (d, 2H, CH$_2$), 3.79 (s, 3H, CH$_3$), 5.08-5.34 (m, 2H), 5.27 (s, 2H, CH$_2$), 5.90-6.05 (m, 1H), 6.40 (s, 1H, pyrimidyl-1H), 7.14-7.47 (m, 4H, Ar—H), 7.66 (s, 1H, CH).

Compound 3 $^1$HNMR (400 MHz, CDCl$_3$): 3.71 (s, 3H, CH$_3$), 3.84 (s, 5H, CH$_3$, CH$_2$), 5.17 (d 1H, CH$_2$), 5.36 (d, 1H, CH$_2$), 5.40 (s, 2H, CH$_2$), 5.95-6.03 (m, 1H, CH), 6.71 (s, 1H, pyrimidyl-H), 7.23 (d, 1H, Ar—H), 7.38-7.40 (m, 2H, Ar—H), 7.52 (d, 1H, Ar—H).

Compound 9 $^1$HNMR (400 MHz, DMSO) δ (ppm): 3.59 (s, 3H, CH$_3$), 3.80-3.84 (d, 2H, CH$_2$), 3.79 (s, 3H, CH$_3$), 5.12-5.30 (m, 2H, CH$_2$), 5.34 (s, 2H, CH$_2$), 5.91-6.01 (m, 1H) 6.73-6.98 (m, 1H, CHF2), 6.81 (s, 1H, pyrimidyl-1H), 7.12-7.50 (m, 4H, Ar—H), 7.64 (s, 1H, CH).

Compound 10 $^1$HNMR (400 MHz, DMSO) δ (ppm): 3.62 (s, 3H, CH$_3$), 3.82 (s, 3H, CH$_3$), 3.91-3.93 (d, 2H, CH$_2$), 5.12-5.14 (d, 1H), 5.36 (s, 2H, CH$_2$), 5.31-5.36 (m, 1H), 5.90-6.00 (m, 1H), 7.05 (s, 1H, pyrimidyl-H), 7.09-7.46 (m, 4H, Ar—H), 7.66 (s, 1H, CH).

Compound 19 $^1$HNMR (400 MHz, DMSO) δ (ppm): 1.70-1.71 (d, 6H, 2CH$_3$), 3.59 (s, 3H, CH$_3$), 3.80-3.81 (d, 2H, CH$_2$), 3.80 (s, 3H, CH$_3$), 5.33-5.35 (m, 1H), 5.37 (s, 2H, CH$_2$), 7.06 (s, 1H, pyrimidyl-H), 7.14-7.47 (m, 4H, Ar—H), 7.65 (s, 1H, CH).

Compound 35 $^1$HMNR (400 MHz, DMSO) δ (ppm): 3.59 (s, 3H, CH$_3$), 3.79 (s, 3H, CH$_3$), 4.14 (s2H, CH$_2$), 5.36 (s, 2H, CH$_2$), 5.38-5.39 (d, 1H, CH$_2$), 5.62 (d, 1H, CH$_2$), 5.59 (d, 1H), 7.09 (s, 1H, pyrimidyl-H), 7.14-7.53 (m, 4H, Ar—H), 7.65 (s, 1H, CH).

Compound 41 $^1$HNMR (400 MHz, DMSO) δ (ppm): 3.59 (s, 3H, CH$_3$), 3.80 (s, 3H, CH$_3$), 4.29 (s2H, CH$_2$), 5.33 (s, 2H, CH$_2$), 5.21 (d, 1H), 5.61 (d, 1H), 5.64 (d, 1H, CH$_2$), 6.73-7.02 (m, 1H, CHF$_2$), 6.89 (s, 1H, pyrimidyl-H), 7.13-7.51 (m, 4H, Ar—H), 7.64 (s, 1H, CH).

Compound 43 $^1$HNMR (400 MHz, DMSO) δ (ppm): 1.15-1.19 (m, 3H, CH$_3$), 2.57-2.63 (m, 2H, CH$_2$), 3.59 (s, 3H, CH$_3$), 3.80 (s, 3H, CH$_3$), 4.14 (s2H, CH$_2$), 5.24 (s, 2H, CH$_2$), 5.33 (d, 1H), 5.57 (d, 1H), 6.47 (s, 1H, pyrimidyl-H), 7.11; 7.65 (s, 1H, CH).

Compound 49 $^1$HNMR (400 MHz, CDCl$_3$) 2.33 (s, 3H, CH$_3$), 3.70 (s, 0.34*3H, CH$_3$), 3.71 (s, 0.66*3H, CH$_3$), 3.76 (d, 0.66*2H, CH$_2$), 3.94 (d, 0.34*2H, CH$_2$), 3.82 (s, 0.34*3H, CH$_3$), 3.83 (s, 0.66*3H, CH$_3$), 5.32 (s, 0.34*2H, CH$_2$), 5.33 (s, 0.66*2H, CH$_2$), 6.01-6.10 (m, 1H), 6.14 (d, 034*2H, CH$_2$), 6.20 (d, 0.66*2H, CH$_2$), 6.28 (s, 0.34*1H, pyrimidyl-H), 6.29 (s, 0.66*1H, pyrimidyl-H), 7.21 (t, 1H, Ar—H), 7.37 (q, 2H, Ar—H), 7.50 (1, 1H, Ar—H), 7.59 (s, 0.34*1H, CH), 7.59 (s, 0.66*1H, CH).

Compound 50 $^1$HNMR (400 Mhz, CDCl$_3$) 3.71 (s, 0.5*3H, CH$_3$), 3.72 (s, 0.5*3H, CH$_3$), 3.79 (d, 0.5*2H, CH$_2$), 3.82 (d, 0.5*2H, CH$_2$), 3.82 (s, 0.5*3H, CH$_3$), 3.83 (s, 0.5*CH$_3$), 3.83 (s, 0.5*3H, CH$_3$), 5.40 (s, 0.5*2H, CH$_2$), 5.41 (s, 0.5*2H, CH$_2$), 6.03-6.10 (m, 1H), 6.19 (d, 0.5*2H, CH$_2$), 6.27 (d, 0.5*2H, CH$_2$), 6.70 (s, 1H, pyrimidyl-H), 7.23-7.25 (m, 1H, Ar—H), 7.37-7.40 (m, 2H, Ar—H), 7.51-7.53 (m, 1H, Ar—H), 7.61 (s, 0.5*1H, CH), 7.62 (s, 0.5*1H, CH).

Compound 51 $^1$HNMR (400 MHz, DMSO) δ (ppm): 3.59 (s, 3H, CH$_3$), 3.79 (s, 3H, CH$_3$), 3.86-3.95 (m, 2H, CH$_2$), 5.36 (s, 2H, C$_2$), 6.04-6.17 (m, 1H, CH), 6.47-6.54 (m, 1H, CH), 7.07 (s, 1H, pyrimidyl-1-H), 7.13-7.52 (m, 4H, Ar—H), 7.66 (s, 1H, CH).

Compound 52 $^1$HNMR (400 MHz, CDCl$_3$): 1.26 (t, 3H, CH$_3$), 2.68 (q, 2H, CH$_2$), 3.71 (s, 3H, CH$_3$), 3.82 (s, 3H, CH$_3$), 4.09 (s, 2H, CH$_2$), 5.40 (s, 2H, CH$_2$), 5.30 (s, 1H, CH$_2$), 5.55 (s, 1H, CH$_2$), 6.75 (s, 1H, pyrimidyl-H), 7.20-7.22 (m, 1H, Ar—H), 7.35-7.38 (m, 2H, Ar—H), 7.52-7.54 (t, 1H, Ar—H).

Compound 55 $^1$HNMR (400 MHz, CDCl$_3$): 0.89-1.12 (m, 4H, cyclopropyl-2CH$_2$), 1.84-1.89 (m, 1H, cyclopropyl-CH), 3.71 (s, 0.5*3H, CH$_3$), 3.72 (s, 0.5*3H, CH$_3$), 3.72 (d, 0.5*2H, CH$_2$), 3.83 (s, 0.5*3H, CH$_3$), 3.84 (s, 0.5*3H, CH$_3$), 3.89 (d, 0.5*2H, CH$_2$), 5.31 (s, 2H, CH$_2$), 6.01-6.09 (m, 1H), 6.14 (d, 0.5*2H, CH$_2$), 6.20 (d, 0.5*2H, CH$_2$), 6.28 (s, 0.5*1H, pyrimidyl-H), 6.29 (s, 0.5*1H, pyrimidyl-H), 7.21 (t, 1H, Ar—H), 7.36 (t, 2H, Ar—H), 7.50 (t, Ar—H), 7.59 (s, 0.5*1H, CH), 7.60 (s, 0.5*1H, CH).

Compound 57 $^1$HNMR (400 MHz, DMSO) δ (ppm): 3.59 (s, 3H, CH$_3$), 3.79 (s, 3H, CH$_3$), 3.84-3.85 (m, 2H, CH$_2$), 5.34 (s, 2H, CH$_2$), 6.06-6.15 (m, 1H, CH), 6.45-6.54 (m, 1H, CH), 6.71-7.03 (m, 1H, CHF$_2$), 6.78 (s, 1H, pyrimidyl-H), 7.13-7.51 (n, 4H, Ar—H), 7.64 (s, 1H, CH).

Compound 65 $^1$HNMR (400 MHz, CDCl$_3$): 2.39 (s, 3H, CH$_3$), 3.71 (s, 3H, CH$_3$), 3.83 (s, 3H, CH$_3$), 3.85 (d, 2H, CH$_2$), 5.32 (s, 2H, CH$_2$), 6.11 (t, 1H, CH), 6.29 (s, 1H, pyrimidyl-H), 7.20-7.22 (m, 1H, Ar—H), 7.35-7.38 (m, 2H, Ar—H), 7.47-7.49 (n, 1H, Ar—H), 7.59 (s, H, CH).

Compound 66 $^1$HNMR (400 MHz, CDCl$_3$): 3.71 (s, 3H, CH$_3$), 3.84 (s, 3H, CH$_3$), 3.88 (d, 2H, CH$_2$), 5.38 (s, 2H, CH$_2$), 6.11 (t, 1H, CH), 6.70 (s, 1H, pyrimidyl-H), 7.21-7.23 (t, 1H, Ar—H), 7.37-7.40 (m, 2H, Ar—H), 7.49-7.51 (m, 1H, Ar—H), 7.60 (s, 1H, CH).

Compound 67 $^1$HNMR (400 MHz, DMSO) δ (ppm): 3.59 (s, 3H, CH$_3$), 3.81 (s, 3H, CH$_3$), 3.84-3.94 (d2H, CH$_2$), 5.37 (s, 2H, CH$_2$), 6.05-6.16 (m, 1H, CH), 7.07 (s, 1H, pyrimidyl-H), 7.10-7.52 (m, 4H, Ar—H), 7.65 (s, 1H, CH).

Compound 68 $^1$HNMR (400 MHz, CDCl$_3$): 1.27 (t, 3H, CH$_3$), 2.67 (q, 2H, CH$_2$), 3.86 (d, 2H, CH$_2$), 3.71; s, 3H, CH$_3$), 3.84 (s, 3H, CH$_3$), 5.32 (s, 2H, CH$_2$), 6.13 (1H, CH), 6.29 (s, 1H, pyrimidyl-H), 7.22 (t, 1H, Ar—H), 7.37 (q, 2H, Ar—H), 7.50 (t, 1H, Ar—H).

Compound 69 $^1$HNMR (400 MHz, CDCl$_3$): 0.98 (t, 3H, CH$_3$), 1.69-1.76 (m, 2H, CH$_2$), 0.98 (t, 2H, CH$_2$), 3.71 (s, 3H, CH$_3$), 3.84 (s, 3H, CH$_3$), 3.86 (d, 2H, CH$_2$), 5.32 (s, 2H, CH$_2$), 6.13 (t, 1H, CH), 6.28 (s, 1H, pyrimidyl-H) 7.21 (t, 1H, Ar—H), 7.37 (1, 2H, Ar—H), 7.50 (t, 1H, AR—H), 7.59 (s, H, CH).

Compound 71 $^1$HNMR (400 MHz, CDCl$_3$): 1.00-1.12 (m, 4H, cyclopropyl-2CH$_2$), 1.87-1.90 (m, 1H, cyclopropyl-CH), 3.71 (s, 3H, CH$_3$), 3.80 (d, 2H, CH$_2$), 3.84 (s, 3H, CH$_3$), 5.30 (s, 2H, CH$_2$), 6.09 (m, 1H, CH), 6.28 (s, 1H, pyrimidyl-H), 7.19-7.21 (m, 1H, Ar—H), 7.35-7.38 (m, 2H, Ar—H), 7.48-7.50 (m, H, Ar—H), 7.59 (s, H, CH).

Compound 81 $^1$HNMR (400 MHz, DMSO) δ (ppm): 2.31 (s, 3H, CH$_3$), 2.63-2.78 (m, 2H, CH$_2$), 3.29-3.34 (m, 2H, CH$_2$), 3.59 (s, 3H, CH$_3$), 3.79 (s, 3H, CH$_3$), 5.28 (s, 2H, CH$_2$), 6.47 (s, 1H, pyrimidyl-H), 7.11-7.44 (m, 4H, Ar—H), 7.63 (s, 1H, CH).

Compound 90 $^1$HNMR (400 MHz, CDCl$_3$): 3.72 (s, 3H, CH$_3$), 3.85 (s, 3H, CH$_3$), 4.14 (s, 2H, CH$_2$), 5.40 (s, 2H, CH$_2$), 6.61 (s, 1H, CH), 6.75 (s, 1H, pyrimidyl-H), 7.24 (d, 1H, Ar—H), 7.36-7.40 (n, 2H, Ar—H), 7.52 (d, 1H, Ar—H), 7.62 (s, 1H, CH).

Compound 114 $^1$HNMR (400 MHz, DMSO) δ (ppm): 2.73-2.81 (n, 2H, CH$_2$), 3.30-3.34 (m, 2H, CH$_2$), 3.59 (s, 3H, CH$_3$), 3.79 (s, 3H, CH$_3$), 5.33 (s, 2H, CH$_2$), 6.71-6.98 (m, 1H, CHF$_2$), 6.83 (s, 1H, pyrimidyl-H), 7.13-7.49 (m, 4H, Ar—H), 7.63 (s, 1H, CH).

Compound 115 $^1$HNMR (400 MHz, DMSO) δ (ppm): 2.72-2.82 (m, 2H, CH$_2$), 3.29-3.34 (m, 2H, CH$_2$) 3.59 (s, 3H, CH$_3$), 3.79 (s, 3H, CH$_3$), 5.28 (s, 2H, CH$_2$), 6.63 (s, 1H, pyrimidyl-H), 7.12-7.46 (m, 4H, Ar—H), 7.67 (s, 1H, CH).

Compound 116 $^1$HNMR (400 MHz, DMSO) δ (ppm): 1.13-1.20 (m, 3H, CH$_3$), 2.57-2.62 (m, 2H, CH$_2$, 2.71-2.80 (m, 2H, CH$_2$), 3.25-3.29 (m, 2H, CH$_3$), 3.59 (s, 3H, CH$_3$), 3.79 (s, 3H, CH$_3$), 5.24 (s, 2H, CH$_2$), 6.45 (s, 1H, pyrimidyl-H), 7.12-7.45 (m, 4H, Ar—H), 7.63 (s, 1H, CH).

Compound 117 $^1$HNMR (400 MHz, DMSO) δ (ppm): 0.86-0.90 (m, 3H, CH$_3$), 1.62-1.71 (m, 2H, CH$_2$), 2.51-2.57 (m, 2H, CH$_2$), 2.72-2.79 (m, 2H, CH$_2$), 3.25-3.28 (m, 2H, CH$_2$), 3.59 (s, 3H, CH$_3$), 3.79 (s, 3H, CH$_3$), 5.23 (s, 2H, CH$_2$), 6.45 (s, 1H, pyrimidyl-H), 7.11-7.46 (m, 4H, Ar—H), 7.63 (s, 1H, CH).

Compound 118 $^1$HNMR (400 MHz, DMSO) δ (ppm): 1.17-1.19 (d, 6H, CH$_3$), 2.50-2.52 (m, H, CH), 2.72-2.83 (m, 2H, CH$_2$), 3.26-3.29 (m, 2H, CH$_2$), 3.58 (s, 3H, CH$_3$), 3.79 (s, 3H, CH$_3$), 5.23 (s, 2H, CH$_2$), 6.45 (s, 1H, pyrimidyl-H), 7.11-7.47 (m, 4H, Ar—H), 7.63 (s, 1H, CH).

Compound 119 $^1$HNMR (400 MHz, DMSO) δ (ppm): 0.98-0.99 (m, 4H, cyclopropyl-2CH$_2$), 1.98-2.01 (m, H, CH), 2.69-2.75 (m, 2H, CH$_2$), 3.20-3.23 (m, 2H, CH$_2$), 3.59 (s, 3H, CH$_3$), 3.79 (s, 3H, CH$_3$), 5.21 (s, 2H, CH$_2$), 6.53 (s, 1H, pyrimidyl-H), 7.11-7.63 (m, 4H, Ar—H), 7.67 (s, 1H, CH).

Compound 127 $^1$HNMR (400 MHz, DMSO) δ (ppm): 1.98 (s, 3H, CH$_3$), 2.31 (s, 3H, CH$_3$), 2.69-2.77 (m, 2H, CH$_2$), 3.22-3.26 (m, 2H, CH$_2$), 3.58 (s, 3H, CH$_3$), 3.79 (s, 3H, CH$_3$), 5.24 (s, 2H, CH$_2$), 7.12-7.51 (in, 4H, Ar—H), 7.62 (s, 1H, CH).

Compound 128 $^1$HNMR (400 MHz, DMSO) δ (ppm): 0.83-0.91 (m, 3H, CH$_3$) 1.27-1.42 (m, 4H, 2CH$_2$), 2.37 (s, 3H, CH$_3$), 2.45-2.51 (m, 2H, CH$_2$), 2.68-2.76 (m, 2H, CH$_2$), 3.22-3.26 (m, 2H, CH$_2$), 3.60 (s, 3H, CH$_3$), 3.80 (s, 3H, CH$_3$), 5.24 (s, 2H, CH$_2$), 7.13-7.45 (m, 4H, Ar—H), 7.66 (s, 1H, CH).

Compound 131 $^1$HNMR (400 MHz, CDCl$_3$): 2.83 (s, 1H, CH), 3.72 (s, 3H, CH$_3$), 3.85 (s, 3H, CH$_3$), 5.13 (d, 2H, CH$_2$), 5.42 (s, 2H, CH$_2$), 6.73 (s, 1H, pyrimidyl-H), 7.23 (t, 1H, Ar—H), 7.39 (q, 2H, Ar—H), 7.49 (t, 1H, Ar—H), 7.60 (s, H, CH).

Compound 145 $^1$HNMR (400 MHz, DMSO) δ (ppm): 2.31 (s, 3H, CH$_3$), 3.73 (s, 3H, CH$_3$), 3.77-3.78 (d, 2H, CH$_2$), 3.91 (s, 3H, CH$_3$), 5.09-5.11 (d, 1H), 5.23 (s, 2H, CH$_2$), 5.27-5.31 (d, 1H), 5.89-5.99 (d, 1H) 6.40 (s, 1H, pyrimidyl-H), 7.23-7.54 (m, 4H, Ar—H).

Compound 146 $^1$HNMR (400 MHz, DMSO) δ (ppm): 3.73 (s, 3H, CH$_3$), 3.81-3.83 (d, 2H, CH$_2$), 3.91 (s, 3H, CH$_3$), 5.12-5.14 (d, 1H), 5.33 (s, 2H, CH$_2$), 5.30-5.35 (m, 1H), 5.90-6.01 (m, 1H), 6.73-7.00 (m, 1H, CHF$_2$), 6.76 (s, 1H, pyrimidyl-H), 7.25-7.64 (m, 4H, Ar—H).

Compound 147 $^1$HNMR (400 MHz, DMSO) δ (ppm): 3.73 (s, 3H, CH$_3$), 3.82-3.84 (d, 2H, CH$_2$), 3.92 (s, 3H, CH$_3$), 5.12-5.14 (d, 1H), 5.36 (s, 2H, CH$_2$), 5.31-5.36 (m, 1H), 5.90-6.00 (m, 1H), 7.05 (s, 1H, pyrimidyl-H), 7.26-7.66 (m, 4H, Ar—H).

Compound 163 $^1$HNMR (400 MHz, CDCl$_3$): 1.77 (s, 6H, 2CH$_3$), 3.88 (s, 3H, CH$_3$), 4.05 (s, 3H, CH$_3$), 3.82 (d, 2H, CH$_2$), 5.36 (s, 2H, CH$_2$), 5.38 (t, 1H, CH), 6.65 (s, 1H, pyrimidyl-H), 7.24 (d, 1H, Ar—H), 7.43-7.48 (m, 2H, Ar—H), 7.53 (d, 1H, Ar—H).

Compound 177 $^1$HNMR (400 MHz, DMSO) δ (ppm): 2.34 (s, 3H, CH$_3$), 3.72 (s, 3H, CH$_3$), 3.91 (s, 3H, CH$_3$), 4.14 (s2H, CH$_2$), 5.23 (s, 2H, CH$_2$), 5.34 (d, 1H), 5.59 (d, 1H), 6.40 (s, 1H, pyrimidyl-H), 7.22-7.57 (m, 4H, Ar—H).

Compound 178 $^1$HNMR (400 MHz, CDCl$_3$): 3.88 (s, 3H, CH$_3$), 4.05 (s, 3H, CH$_3$), 4.08 (s, 2H, CH$_2$), 5.34 (d, 1H, CH$_2$), 5.57 (d, 1H, CH$_2$), 5.35 (s, 2H, CH$_2$), 6.65 (s, 1H, pyrimidyl-H), 7.24 (d, 1H, Ar—H), 7.43-7.49 (m, 2H, Ar—H), 7.54 (d, 1H, Ar—H).

Compound 179 $^1$HNMR (400 MHz, DMSO) δ (ppm): 3.74 (s, 3H, CH$_3$), 3.92 (s, 3H, CH$_3$), 4.20 (s, 2H, CH$_2$) 5.37 (s, 2H, CH$_2$), 5.38-5.39 (d, 1H, CH$_2$), 5.62 (d, 1H, CH$_2$), 5.59 (d, 1H), 7.09 (s, 1H, pyrimidyl-H) 7.26-7.61 (m, 4H, Ar—H).

Compound 180 $^1$HNMR (400 MHz, DMSO) δ (ppm): 1.15-1.19 (m, 3H, CH$_3$), 2.58-2.64 (m, 2H, CH$_2$), 3.74 (s, 3H, CH$_3$), 3.91 (s, 2H, CH$_2$), 4.15 (s, 2H, CH$_2$), 5.24 (s, 2H, CH$_2$), 5.34 (d, 1H), 5.59 (d, 1H), 6.41 (s, 1H, pyrimidyl-H), 7.23-7.55 (m, 4H, Ar—H).

Compound 191 $^1$HNMR (400 MHz, DMSO) δ (ppm): 1.94 (s, 3H, CH$_3$), 2.32 (s, 3H, CH$_3$), 3.72 (s, 3H, CH$_3$), 3.91 (s, 3H, CH$_3$), 4.11 (s2H, CH$_2$), 5.24 (s, 2H, CH$_2$), 5.33 (d, 1H), 5.58 (d, 1H), 6.40 (s, 1H, pyrimidyl-H), 7.25-7.58 (m, 4H, Ar—H).

Compound 193 $^1$HNMR (400 MHz, CDCl$_3$) 2.37 (s, 3H, CH$_3$), 3.76 (d, 0.6*2H, CH$_2$), 3.94 (d, 0.4*2H, CH$_2$), 3.86 (s, 0.6*3H, CH$_3$), 3.87 (s, 0.4*3H, CH$_3$), 4.03 (s, 0.6*3H, CH$_3$), 4.04 (s, 0.4*3H, CH$_3$), 5.30 (s, 2H, CH$_2$), 6.14 (d, 0.4*1H, CH), 6.21 (d, 0.6*1H, CH), 6.28 (s, 0.4*1H, pyrimidyl-H), 6.29 (s, 0.6*1H, pyrimidyl-H), 7.22 (d, 1H, Ar—H), 7.40-7.47 (m, 2H, Ar—H), 7.50 (d, 1H, Ar—H).

Compound 194 $^1$HNMR (400 MHz, DMSO) δ (ppm): 3.78 (s, 3H, CH$_3$), 4.03 (s, 0.3*:3H, CH$_3$), 4.04 (d, 0.7*2H, CH$_2$), 3.78 (d, 0.7*2H, CH$_2$), 3.95 (d, 0.3*2H, CH$_2$) 6.01-6.07 (m, 1H), 6.18 (d, 0.3*2H, CH$_2$), 6.26 (d, 0.7*2H, CH$_2$), 6.41 (t, 1H, CHF$_2$), 6.65 (s, 1H, pyrimidyl-H), 7.24 (d, 1H, Ar—H), 7.42-7.51 (m, 2H, Ar—H), 7.54 (d, 1H, AR—H)

Compound 195 $^1$HNMR (400 MHz, DMSO) δ (ppm): 3.74 (s, 3H, CH$_3$), 3.94 (s, 3H, CH$_3$), 3.86-3.95 (m, 2H, CH$_2$) 5.37 (s, 2H, CH$_2$), 6.04-6.17 (m, 1H, CH), 6.47-6.54 (m, 1H, CH), 7.07 (s, 1H, pyrimidyl-H), 7.26-7.59 (m, 4H, Ar—H).

Compound 199 $^1$HNMR (400 MHz, CDCl$_3$): 0.96-1.11 (m, 4H, cyclopropyl-2CH$_2$), 1.83-1.87 (m, 1H, cyclopropyl-CH), 3.86 (s, 3H, CH$_3$), 4.02 (s, 0.5*3H, CH$_3$), 4.03 (d, 0.5*2H, CH$_2$), 3.70 (d, 0.5*2H, CH$_2$), 3.87 (d, 0.5*2H, CH$_2$), 5.98-6.06 (m, 1H), 6.14 (d, 0.5*2H, CH$_2$), 6.18 (d, 0.5*2H, CH$_2$), 6.24 (s, 0.5*1H, pyrimidyl-H), 6.25 (s, 0.5*1H, pyrimidyl-H), 7.21 (t, 1H, Ar—H), 7.38-7.45 (m, 2H, Ar—H), 7.50 (d, 1H, Ar—H).

Compound 209 $^1$HNMR (400 MHz, CDCl$_3$): 2.38 (s, 3H, CH$_3$), 3.85 (d, 2H, CH$_2$), 3.86 (s, 3H, CH$_3$), 4.04 (s, 3H, CH$_3$), 5.30 (s, 2H, CH$_2$), 6.11 (1H, CH), 7.22 (d, 1H, Ar—H), 7.40-7.46 (m, 2H, Ar—H), 7.51 (t, 1H, Ar—H)

Compound 210 $^1$HNMR (400 MHz, CDCl$_3$) 3.88 (s, 3H, CH$_3$), 4.04 (s, 3H, CH$_3$), 3.88 (d, 2H, CH$_2$), 5.35 (s, 2H, CH$_2$), 6.10 (t, 1H, CH), 6.66 (s, 1H, pyrimidyl-H), 7.24 (d, 1H, Ar—H), 7.43-7.7.48 (m, 2H, Ar—H), 7.50 (d, 1H, Ar—H)

Compound 211 $^1$HNMR (400 MHz, CDCl$_3$): 3.88 (s, 3H, CH$_3$), 4.05 (s, 3H, CH$_3$), 3.89 (d, 2H, CH$_2$), 5.37 (s, 2H, CH$_2$), 6.70 (s, 1H, pyrimidyl-H), 7.25 (d, 1H, Ar—H), 7.44-7.49 (m, 2H, Ar—H), 7.53 (d, 1H, Ar—H)

Compound 212 $^1$HNMR (400 MHz, CDCl$_3$): 1.26 (3H, CH$_3$), 2.66 (q, 2H, CH$_2$), 3.85 (d, 2H, CH$_2$), 3.86 (s, 3H, CH$_3$), 4.03 (s, 3H, CH$_3$), 5.30 (s, 2H, CH$_2$), 6.11 (1, 1H, CH), 6.25 (s, 1H, pyrimidyl-H), 7.22 (d, 1H, Ar—H), 7.40-7.46 (m, 2H, Ar—H), 7.51 (1, 1H, Ar—H).

Compound 213 $^1$HNMR (400 MHz, CDCl$_3$): 0.98 (t, 3H, CH$_3$), 1.69-11.76 (m, 2H, CH$_2$), 2.60 (t 2H, CH$_2$), 3.86 (d, 2H, CH$_2$), 3.87 (s, 3H, CH$_3$), 4.04 (s, 3H, CH$_3$), 5.30 (s, 2H, CH$_2$), 6.11 (t, 1H, CH), 6.24 (s, 1H, pyrimidyl-H), 7.23 (d, 1H, Ar—H), 7.43-7.47 (m, 2H, Ar—H), 7.51 (d, 1H, Ar—H)

Compound 215 $^1$HNMR (400 MHz, CDCl$_3$): 1.00-1.12 (m, 4H, cyclopropyl-2CH$_2$), 1.84-1.87 (m, 1H, cyclopropyl-CH), 3.87 (s, 3H, CH$_3$), 3.79 (d, 2H, CH$_2$), 4.04 (s, 3H, CH$_3$), 5.30 (s, 2H, CH$_2$), 6.08 (1, 1H, CH), 6.27 (s, 1H, pyrimidyl-H), 7.22 (d, 1H, Ar—H), 7.40-7.46 (m, 2H, Ar—H), 7.50 (d, 1H, Ar—H).

Compound 257 $^1$HNMR (400 MHz, CDCl$_3$): 2.70-2.82 (m, 2H, CH$_2$), 3.28 (1, 2H, CH$_2$), 3.86 (s, 3H, CH$_3$), 4.02 (s, 3H, CH$_3$), 5.29 (s, 2H, CH$_2$), 6.24 (s, 1H, pyrimidyl-H), 7.23 (d, 1H, Ar—H), 7.41-7.47 (m, 2H, Ar—H), 7.50 (d, H, Ar—H).

Compound 258 $^1$HNMR (400 MHz, CDCl$_3$): 2.73-2.80 (m, 2H, CH$_2$), 3.31 (1, 2H, CH$_2$), 3.88 (s, 3H, CH$_3$), 4.04 (s, 3H, CH$_3$), 5.35 (s, 2H, CH$_2$), 6.40 (t, 1H, CHF$_2$), 6.65 (s, 1H-pyrimidyl-H), 7.25 (d, 1H, Ar—H), 7.43-7.48 (m, 2H, Ar—H), 7.53 (d, H, Ar—H).

Compound 259 $^1$HNMR (400 MHz, CDCl$_3$): 2.74-2.83 (m, 2H, CH$_2$), 3.33 (t, 2H, CH$_2$), 3.88 (s, 3H, CH$_3$), 4.04 (s, 3H, CH$_3$), 5.36 (s, 2H, CH$_2$), 6.69 (s, 1H, pyrimidyl-H), 7.25 (d, 1H, Ar—H), 7.44-7.49 (m, 2H, Ar—H), 7.53 (d, H, Ar—H).

Compound 260 $^1$HNMR (400 MHz, DMSO) δ (ppm): 1.15-1.19 (m, 3H, CH$_3$), 2.57-2.63 (m, 2H, CH$_2$), 2.73-2.82 (m, 2H, CH$_2$), 3.27-3.30 (m, 2H, CH$_2$), 3.73 (s, 3H, CH$_3$), 3.90 (s, 3H, CH$_3$), 5.23 (s, 2H, CH$_2$), 6.40 (s, 1H, pyrimidyl-H), 7.23-7.54 (m, 4H, Ar—H).

Compound 261 $^1$HNMR (400 MHz, DMSO) δ (ppm): 0.86-0.90 (m, 3H, CH$_3$), 1.62-1.67 (m, 2H, CH$_2$), 2.51-2.57 (m, 2H, CH$_2$), 2.74-2.80 (m, 2H, CH$_2$), 3.25-3.28 (m, 2H, CH$_2$), 3.72 (s, 3H, CH$_3$), 3.89 (s, 3H, CH$_3$), 5.22 (s, 2H, CH$_2$), 6.40 (s, 1H, pyrimidyl-H), 7.24-7.54 (m, 4H, Ar—H)

Compound 262 $^1$HNMR (400 MHz, DMSO) δ (ppm): 1.17-1.19 (d, 6H, CH$_3$), 2.75-2.89 (m, 3H, CH, CH$_2$), 3.26-3.29 (m, 2H, CH$_2$), 3.78 (s, 3H, CH$_3$), 3.90 (s, 3H, CH$_3$), 5.22 (s, 2H, CH$_2$), 6.40 (s, 1H, pyrimidyl-H), 7.24-7.55 (m, 4H, Ar—H)

Compound 263 $^1$HNMR (400 MHz, DMSO) δ (ppm): 0.98-1.00 (m, 4H, cyclopropyl-2CH$_2$), 1.98-2.05 (m, H, CH), 2.69-2.79 (m, 2H, CH$_2$), 3.21-3.24 (in, 2H, CH$_2$), 3.74 (s, 3H, CH$_3$), 3.90 (s, 3H, CH$_3$), 5.20 (s, 2H, CH$_2$), 6.48 (s, 4H, Ar—H).

Compound 271 $^1$HNMR (400 MHz, DMSO) δ (ppm): 2.07 (s, 3H, CH$_3$), 2.34 (s, 3H, CH$_3$), 2.71-2.79 (m, 2H, CH$_2$), 3.23-3.26 (m, 2H, CH$_2$), 3.71 (s, 3H, CH$_3$), 3.90 (s, 3H, CH$_3$), 5.24 (s, 2H, CH$_2$), 7.24-7.54 (m, 4H, Ar—H).

Compound 272 $^1$HNMR (400 MHz, DMSO) δ (ppm): 0.84-0.87 (m, 3H, CH$_3$), 1.25-1.38 (m, 2H, 2CH$_2$), 2.34 (s, 3H, CH$_3$), 2.42-2.46 (m, 2H, CH$_2$), 2.69-2.79 (m, 2H, CH$_2$), 3.23-3.27 (m, 2H, CH$_2$), 3.72 (s, 3H, CH$_3$), 3.91 (s, 3H, CH$_3$), 5.24 (s, 2H, CH$_2$), 7.25-7.54 (m, 4H, Ar—H).

Compound 238 $^1$HNMR (400 MHz, DMSO) δ (ppm): 3.75 (s, 3H, CH$_3$), 3.92 (s, 3H, CH$_3$), 3.84-3.94 (m, 2H, CH$_2$), 5.50 (s, 2H, CH$_2$), 6.06-6.15 (m, 1H, CH), 6.44-6.54 (m, 1H, CH), 6.87-7.03 (m, 1H, CHF$_2$), 6.94 (s, 1H, pyrimidyl-H), 7.45-7.59 (m, 4H, Ar—H).

Compound 353 $^1$HNMR (400 MHz, DMSO) δ (ppm): 2.34 (s, 3H, CH$_3$), 3.66 (s, 3H, CH$_3$), 3.68 (s, 3H, C$_3$), 3.83-3.85 (d, 2H, CH$_2$), 5.41 (s, 2H, CH$_2$), 6.23-6.26 (m, 1H, CH), 6.59 (s 1H, pyrimidyl-H), 7.40-7.46 (m, 4H, Ar—H).

Compound 354 $^1$HNMR (400 MHz, DMSO) δ (ppm): 3.66 (s, 3H, CH$_3$), 3.68 (s, 3H, CH$_3$), 3.89-3.91 (d, 2H, CH$_2$), 5.50 (s, 2H, CH$_2$), 6.28-6.32 (m, 1H, CH), 6.74-7.01 (m, 1H, CHF$_2$) 6.96 (s, 1H, pyrimidyl-H), 7.41-7.58 (m, 4H, Ar—H).

Compound 404 $^1$HNMR (400 MHz, DMSO) δ (ppm): 1.16-1.20 (m, 3H, CH$_3$) 2.59-2.63 (m, 2H, CH$_2$), 2.72-2.82 (m, 2H, CH$_2$), 3.27-3.31 (m, 2H, CH$_2$), 3.67 (s, 3H, CH$_3$), 3.69 (s, 3H, CH$_3$), 5.41 (s, 2H, CH$_2$), 6.55 (s, 1H, pyrimidyl-H), 7.42-7.56 (m, 4H, Ar—H).

Compound 405 $^1$HNMR (400 MHz, DMSO) δ (ppm): 0.87-0.91 (m, 3H, CH$_3$), 1.62-1.69 (m, 2H, CH$_2$), 2.55-2.59 (m, 2H, CH$_2$), 2.73-2.82 (m, 2H, CH$_2$), 3.27-3.31 (m, 2H, CH$_2$), 3.66 (s, 3H, CH$_3$), 3.69 (s, 3H, CH$_3$), 5.41 (s, 2H, CH$_2$), 6.54 (s, 1H, pyrimidyl-H) 7.41-7.59 (m, 4H, Ar—H).

Compound 406 $^1$HNMR (400 MHz, DMSO) δ (ppm): 1.18-1.20 (d, 6H, 2CH$_3$) 1.98-2.01 (m, H, CH), 2.75-2.90 (m, 2H, CH$_2$), 3.28-3.32 (m, 2H, CH$_2$), 3.66 (s, 3H, CH$_3$), 3.69 (s, 3H, CH$_3$), 5.40 (s, 2H, CH$_2$), 6.54 (s, 1H, pyrimidyl-H), 7.40-7.59 (m, 4H, Ar—H).

Compound 407 $^1$HNMR (400 MHz, DMSO) δ (ppm): 0.99-1.02 (m, 4H, cyclopropyl-2CH$_2$), 1.98-2.01 (m, H, CH), 1.98-2.01 (m, H, CH), 2.75-2.90 (m, 2H, CH$_2$), 3.20-3.35 (m, 2H, CH$_2$), 3.66 (s, 3H, CH$_3$), 3.69 (s, 3H, CH$_3$), 5.34 (s, 2H, CH$_2$), 6.53 (s, 1H, pyrimidyl-H), 7.41-7.59 (m, 4H, Ar—H).

PREPARATION EXAMPLES

The addition amount of each component is a weight percentage. The active ingredient in formulation can be selected from any of the compounds of formula (I) of the present invention and the addition amount of which is calculated by multiplying weight by purity.

Example 5

30% Wettable Powder

| | |
|---|---|
| Compound 81 | 30% |
| Sodium dodecyl sulfate | 2% |
| Sodium lignostilionate | 3% |
| Naphthalenesulfonic acid formaldehyde condensate | 5% |
| Light calcium carbonate | up to 100% |

The compound and other components were fully mixed, and crushed by an ultrafine pulverizer to obtain 30% wettable powder product.

Example 6

40% Suspension Concentrate

| | |
|---|---|
| Compound 81 | 40% |
| Ethylene glycol | 10% |
| Nonylphenol polyglycol ether | 6% |
| Sodium lignosulfonate | 10% |
| Carboxymethyl cellulose | 1% |
| 37% formaldehyde solution | 0.2% |
| 75% silicone oil emulsion | 0.8% |
| Water | up to 100% |

The compound and other components were fully mixed to obtain the suspension concentrate, which can be diluted with water to obtain a diluent at any required concentration.

Example 7

60% Water-Dispersible Granules

| | |
|---|---|
| Compound 81 | 60% |
| Sodium naphthalene sulfonate formaldehyde condensate | 12% |
| N-methyl-N-oleoyl-taurate sodium | 8% |
| Polyvinylpyrrolidone | 2% |
| Carboxymethyl cellulose | 2% |
| Kaolin | up to 100% |

The compound and other components were mixed and pulverized, then kneaded with water, granulated in a granulator with a 10-100 mesh sieve, then dried and sieved according to sieve range to obtain 60% water-dispersible granules.

(1) Testing Examples of Biological Activity

Activity test experiments of the compound of the present invention against adults of *Tetranychus cinnabarinus* were carried out. The test methods are as follow:

Example 8

Insecticidal Activity Test

A certain amount of the original drug was weighed by an analytical balance (0.0001 g), and dissolved in DMF containing 1% Tween-80 emulsifier to prepare a 1% mother liquor, which was then diluted with distilled water for later use.

The insecticidal efficacy was evaluated by a leaf-dipping method with the armyworm as a target and a spray method with *Tetranychus cinnabarinus* and *Aphis craccivora* Koch as a target.

Activity Test of Armyworm

Leaf-dipping method: the target for the test was the armyworm, and corn leaves in an appropriate amount were fully infiltrated in the prepared liquid, then dried naturally, placed in culture dishes with filter papers, inoculated with 3rd instar larvae of the armyworm at 10 heads/dish, and placed in an observation room and cultured at 24~27° C. the results were investigated after 3 days. A brush was used to touch the insect bodies, and the unresponsive were regarded as dead insects.

Partial Test Results are as Follow:

At a test concentration of 500 mg/L, compounds 1, 49, 50, 55, 65, 68, 71, 114, 115, 131, 163, 191, 195, 209, 210, 212, 262, 263, 272, 339, 358, 404, 407 had a lethal rate of more than 80% on aphids;

Compounds 9, 34, 35, 36, 51, 67, 113, 116, 118, 117, 119, 128, 145, 147, 178, 179, 180, 193, 194, 199, 211, 213, 214, 215, 260 261, 271, 337, 338, 353,354, 356, 357, 359, 405, 406, 549 had a lethal rate of 100% on aphids;

Compounds 68, etc at 100 mg/L had a lethal rate of more than 80% on aphids.

Example 9

Activity Test of *Tetranychus Cinnabarinus* and Aphis Craccivora Koch

Spray method: the target for the test was *Tetranychus cinnabarinus* and Aphis craccivora Koch, that is, broad bean leaves inoculated with *Tetranychus cinnabarinus* and Aphis craccivora Koch, respectively, were placed under the spray treatment of Potter spray tower. After the treatment, the *Tetranychus cinnabarinus* were placed in an observation room and cultured at 24~27° C., the Aphis craccivora Koch was placed in an observation room and cultured at 20~22° C., and the results were investigated after 2 days. A brush was used to touch the insect body, and the unresponsive were regarded as dead insects.

1̂ Activity Assay of *Tetranychus Cinnabarinus*

At the test concentration of 500 mg/L, the lethal rate of compounds 19, 34, 49, 55, 114, 128, 179, 261, 263, 339 on. *Tetranychus cinnabarinus* was more than 80%; the lethal rate of compounds 9, 10, 35, 51, 67, 113, 116, 117, 118, 119, 260, 262, 50, 1, 55, 127, 147, etc. on *Tetranychus cinnabarinus* was more than 100%.

At the concentration of 100 mg/L, the lethal rite of compounds 10, 1, 49, 55, 113, 119, 147, 179, etc. on *Tetranychus cinnabarinus* was more than 50%; the lethal rate of compounds 116, 117, 118, 35, 67, 50, 9, 127, 128, 51, 34, 19, etc. on *Tetranychus cinnabarinus* was more than 80%.

At the concentration of 20 mg/l the lethal rate of compounds 1, 34, 35, etc. on *Tetranychus cinnabarinus* was more than 50%; the lethal rate of compounds 9, 19, 51, 67, 128, etc. on *Tetranychus cinnabarinus* was more than 80%.

2̂ Activity Assay of Aphis Craccivora Koch

At the test concentration of 500 mg/L, the lethal rate of compounds 113, 116, 119 on Aphis craccivora Koch was more than 80%.

(2) Test Example of Living Protection Activity

Example 10

Prevention Experiment of Powdery Mildew of Cucumber

Experimental Method was as Follows:

The living pot assay method was adopted, that is, the sample of the test compound was dissolved with a small amount of DMF solvent (the kind of solvent such as acetone, methanol, DMF, etc., is selected according to the solvency of the sample, and the volume ratio of the solvent amount to the spray amount is equal to or less than 0.05), diluted with water containing 0.1% Tween 80, and formulated into the test solution with a desired concentration. Cucumber seedlings at leaf period with the same growth period was sprayed evenly with the prepared agent, and aired. Each concentration was one treatment, each treatment was repeated 3 times, a control agent and a water of blank control were set separately. The fresh powdery mildew spores on the leaves of cucumbers were washed and filtered with double gauze to prepare a suspension with a concentration of about 100,000 spores/mL. The samples were inoculated by spraying, the inoculated samples were moved into artificial climate, and relative humidity was maintained at 60-70%, the temperature was maintained at 23° C., after about 10 days, grading investigation was carried out according to the morbidity of the blank control, control effect was calculated according to disease index.

Test results of living protection activity of partial compounds were as follows:

At a concentration of 200 ppm, compounds 10, 19, 128, 147, 163, 195, 210, 211, 212, 257, 258, 259, 401, 402, etc. had an effect of preventing powdery mildew by more than 80%; compounds 1, 9, 34, 35, 36, 49, 50, 51, 55, 67, 113, 114, 127, 128, 146, 177, 178, 179, 180, 191, 193, 194, 199, 271, etc. had an effect of preventing powdery mildew by 100%.

At a concentration of 100 ppm, compounds 1, 51, 36, 55, 113, 114, 258, 218, 194, 146, 147, 177, 178, 191 had an effect of preventing powdery mildew by more than 50%; compounds 9, 35, 49 50, 127, 195, 212, 271, etc. had an effect of preventing powdery mildew effect by more than 80%;

At a concentration of 50 ppm, compounds 9, 50, 127, etc. had an effect of preventing powdery mildew by more than 80%.

(3) Testing Example of Acaricidal Activity of Partial Compounds and Control Compounds Experimental Methods were as Follows:

Spray method: the test target was *Tetranychus cinnabarinus*, that is, broad bean leaves inoculated with adults of *Tetranychus cinnabarinus* were placed under the spray treatment of Potter spray towers. After treatment, the *Tetranychus cinnabarinus* was placed in an observation room and cultured at 25~27° C., and the results were investigated after 48 hours. The brush was used to touch the insect body, and the unresponsive were regarded as dead insects. The test concentrations of the compounds on killing cinnabarin were 50, 25, 12.5, 6.25, 3.125 mg/L.

Egg test: each treated broad bean leave was inoculated with 10 adults of *Tetranychus cinnabarinus*, and the adults were removed after the eggs were laid for 24 hours. The leaves with eggs were sprayed under Potter spray towers. After treatment, the eggs of *Tetranychus cinnabarinus* were placed in an observation room and cultured at 25~27° C. And the test was examined until the eggs under the blank treatment completely hatched out. The concentration of the compound that kills the eggs of *Tetranychus cinnabarinus* was 100, 50, 25, 12.5, 6.25 mg/L.

Nymph test: broad bean leaves were inoculated with 10 adult mites, and the adults were removed after laying eggs for 24 hours. The eggs were fed in insect rearing room, and when they hatched into nymphs, they were sprayed with a sprayer. After treatment, the leaves with the nymphs were placed in an observation room and cultured at 25-27° C., and the results were investigated after 48 hours. A brush was used to touch the insect bodies, and the unresponsive were regarded as the dead. The test concentrations of the compound on killing cinnabarin were 5, 2.5, 1.25, 0.625, 0.3125 mg/L.

The comparison test results were as follows:

In the cases where compound 67 and fluacrypyrim were given at a concentration of 50, 25, and 12.5 mg/L, respectively, the lethal rate of compound 67 against adult mites was better than that of fluacrypyrim.

In the cases where compound 67 and fluacrypyrim were given at a concentration of 100, 50, 25, 12.5, 6.25 mg/L, respectively, the lethal rate of compound 67 on eggs of Tetranychus cinnabarinus was better than that of fluacrypyrim.

In the cases where compound 67 and fluacrypyrim were given at a concentration of 5, 2.5, 1.25, 0.625, 0.3125 mg/L, respectively, the lethal rate of compound 67 on nymphs of Tetranychus cinnabarinus was better than that of fluacrypyrim.

TABLE 5 toxicity test data of compound 67 and fluacrypyrim on adults of Tetranychus cinnabarinus

| Agent | Concentration (mg/L) | Mortality (%) |
|---|---|---|
| 67 | 50 | 92.41 |
|  | 25 | 81.06 |
|  | 12.5 | 70.83 |
|  | 6.25 | 61.94 |
|  | 3.125 | 30.19 |
| Fluacrypyrim | 50 | 88.89 |
|  | 25 | 75.94 |
|  | 12.5 | 70.59 |
|  | 6.25 | 64.58 |
|  | 3.125 | 39.55 |
| CK | — | 7.69 |

TABLE 6 toxicity test data of compound 67 and fluacrypyrim on eggs of Tetranychus cinnabarinus

| Agent | Concentration (mg/L) | Mortality (%) |
|---|---|---|
| 67 | 100 | 93.14 |
|  | 50 | 81.10 |
|  | 25 | 65.61 |
|  | 12.5 | 33.14 |
|  | 6.25 | 15.13 |
| Fluactypyrim | 100 | 75.00 |
|  | 50 | 54.86 |
|  | 25 | 32.16 |
|  | 12.5 | 13.59 |
|  | 6.25 | 10.84 |
| CK | — | 12.02 |

TABLE 7 toxicity test data of compound 67 and fluacrypyrim on nymphs of Tetranychus cinnabarinus

| Agent | Concentration (mg/L) | Mortality (%) |
|---|---|---|
| 67 | 5 | 90.32 |
|  | 2.5 | 73.08 |
|  | 1.25 | 53.99 |

TABLE 7-continued toxicity test data of compound 67 and fluacrypyrim on nymphs of Tetranychus cinnabarinus

| Agent | Concentration (mg/L) | Mortality (%) |
|---|---|---|
|  | 0.625 | 26.22 |
|  | 0.3125 | 15.00 |
| Fluacrypyrim | 5 | 82.48 |
|  | 2.5 | 55.29 |
|  | 1.25 | 28.76 |
|  | 0.625 | 17.14 |
|  | 0.3125 | 7.74 |
| CK | — | 4.76 |

The invention claimed is:

1. A substituted pyrimidine thioether compound as shown in formula (I):

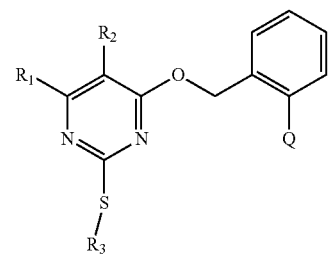

in formula (I):

$R_1$ is selected from the group consisting of hydrogen, halogen, $C_1$-$C_{12}$ alkyl, $C_3$-$C_{12}$ cycloalkyl, halogenated $C_1$-$C_{12}$ alkyl and $C_1$-$C_{12}$ alkoxy;

$R_2$ is selected from the group consisting of hydrogen, halogen, nitro, cyano, $C_1$-$C_{12}$ alkyl, halogenated $C_1$-$C_{12}$ alkyl and $C_1$-$C_{12}$ alkoxy;

$R_3$ is selected from the group consisting of $C_2$-$C_{12}$ alkenyl, halogenated $C_2$-$C_{12}$ alkenyl, $C_2$-$C_{12}$ alkynyl, halogenated $C_2$-$C_{12}$ alkynyl and $C_3$-$C_{12}$ cycloalkenyl;

and Q is a group selected from $Q_1$-$Q_7$, $Q_{10}$, $Q_{11}$, $Q_{13}$ and $Q_{14}$:

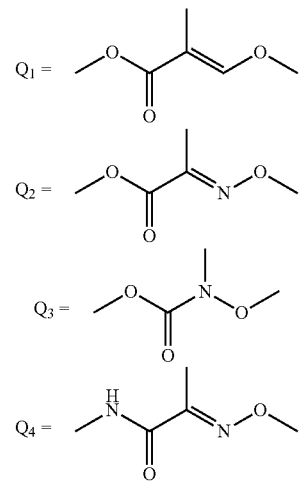

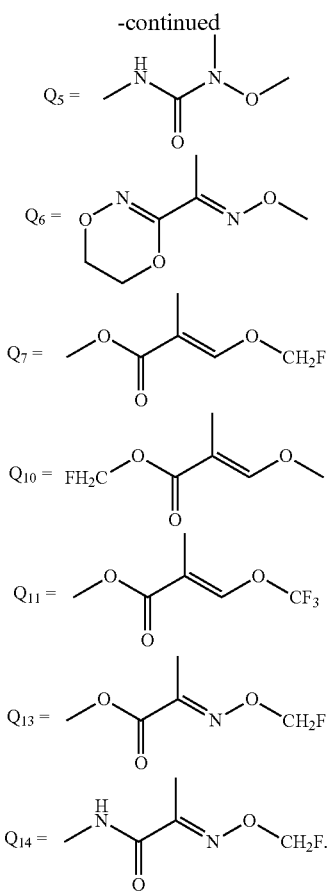

2. The substituted pyrimidine thioether compound as claimed in claim 1, wherein
   $R_1$ is selected from the group consisting of hydrogen, halogen, $C_1$-$C_6$ alkyl, $C_3$-$C_8$ cycloalkyl, halogenated $C_1$-$C_6$ alkyl and $C_1$-$C_6$ alkoxy;
   $R_2$ is selected from the group consisting of hydrogen, halogen, nitro, cyano, $C_1$-$C_6$ alkyl, halogenated $C_1$-$C_6$ alkyl and $C_1$-$C_6$ alkoxy;
   $R_3$ is selected from the group consisting of $C_2$-$C_6$ alkenyl, halogenated $C_2$-$C_6$ alkenyl, $C_2$-$C_6$ alkynyl, halogenated $C_2$-$C_6$ alkynyl and $C_3$-$C_6$ cycloalkenyl.

3. The substituted pyrimidine thioether compound as claimed in claim 2, wherein
   $R_1$ is selected from the group consisting of hydrogen, halogen, $C_1$-$C_4$ alkyl, $C_3$-$C_6$ cycloalkyl, halogenated $C_1$-$C_4$ alkyl and $C_1$-$C_4$ alkoxy;
   $R_2$ is selected from the group consisting of hydrogen, halogen, nitro, cyano, $C_1$-$C_4$ alkyl, halogenated $C_1$-$C_4$ alkyl and $C_1$-$C_4$ alkoxy;
   $R_3$ is selected from the group consisting of $C_2$-$C_6$ alkenyl, halogenated $C_2$-$C_6$ alkenyl, $C_2$-$C_6$ alkynyl, halogenated $C_2$-$C_6$ alkynyl and $C_3$-$C_6$ cycloalkenyl;
   and Q is a group selected from $Q_1$-$Q_7$.

4. The substituted pyrimidine thioether compound as claimed in claim 3, wherein
   $R_1$ is hydrogen, chlorine, bromine, methyl, ethyl, n-propyl, isopropyl, cyclopropyl, n-butyl, isobutyl, tert-butyl, monofluoromethyl, monochloromethyl, difluoromethyl, trifluoromethyl or trifluoroethyl;
   $R_2$ is hydrogen, fluorine, chlorine, bromine, cyano, nitro, methyl, ethyl, n-propyl, isopropyl, n-butyl, isobutyl, methoxy, ethoxy or trifluoroethoxy;
   $R_3$ is $CH_2$=$CHCH_2$, $(CH_3)_2C$=$CHCH_2$, $CH_3CH$=$CHCH_2$, $CHCl$=$CHCH_2$, $CH_2$=$CClCH_2$, $CHCl$=$CClCH_2$, $CCl_2$=$CHCH_2$, $CCl_2$=$CClCH_2$, $CF_2$=$CFCH_2$, $CF_2$=$CFCH_2CH_2$, $CH$≡$CCH_2$ or $CH_3C$≡$CCH_2$;
   Q is a group selected from $Q_1$-$Q_6$.

5. The substituted pyrimidine thioether compound as claimed in claim 4, wherein
   $R_1$ is methyl, ethyl, n-propyl, isopropyl, cyclopropyl, difluoromethyl or trifluoromethyl;
   $R_2$ is hydrogen, chlorine, nitro, methyl or n-butyl;
   $R_3$ is $CH_2$=$CHCH_2$, $(CH_3)_2C$=$CHCH_2$, $CH_3CH$=$CHCH_2$, $CHCl$=$CHCH_2$, $CH_2$=$CClCH_2$, $CHCl$=$CClCH_2$, $CCl_2$=$CHCH_2$, $CCl_2$=$CClCH_2$, $CF_2$=$CFCH_2CH_2$, $CH$≡$CCH_2$ or $CH_3C$≡$CCH_2$;
   Q is a group selected from $Q_1$-$Q_4$.

6. A preparation method of the substituted pyrimidine thioether compound represented by formula (I) as claimed in claim 1,
   where Q in the compound of formula (I) is selected from any one of $Q_1$, $Q_2$, $Q_3$, $Q_6$, $Q_7$, $Q_{10}$, $Q_{11}$ and $Q_{13}$,
   the method comprises:
   reacting a hydroxyl-containing pyrimidine compound of formula (III) and benzyl halide of formula (IV) in the presence of an alkaline material and an organic solvent at a temperature ranging from 20 to 100° C. for 0.5 to 20 hours;
   performing separation and purification to obtain the corresponding substituted pyrimidine thioether compound of formula (I); wherein a molar ratio of the compound of formula (III) to the compound of formula (IV) ranges from 1:1 to 1:1.1;

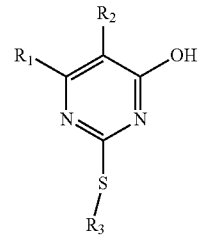

III

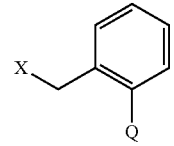

IV in formula (III) or formula (IV), $R_1$, $R_2$, $R_3$ and Q have the same definitions with that of formula (I), X is a leaving group selected between chlorine and bromine;
where Q in the compound of formula (I) is selected from $Q_4$, $Q_5$ or $Q_{14}$, the method further comprises:
reacting the compound of formula (I) in which Q is respectively $Q_2$, $Q_3$ or $Q_{13}$ with a methylamine aqueous solution to obtain the compound of formula (I) in which Q is $Q_4$, $Q_5$ or $Q_{14}$, respectively; wherein a mass concentration of the methylamine aqueous solution is between 20% and 60%; a molar ratio of the compound of formula (I) in which Q is $Q_2$, $Q_3$ or $Q_{13}$ to methylamine in the methylamine aqueous solution ranges from 1:5 to 1:10.

7. The method as claimed in claim 6, wherein the organic solvent is tetrahydrofuran, cyclopentyl methyl ether acetonitrile, xylene, chlorobenzene, DMF, N,N-dimethylacetamide, DMSO, acetone, butanone, methyl isobutyl ketone or methyl tert-butyl ether.

8. The method as claimed in claim 6, wherein the alkaline material is selected from potassium hydroxide, sodium hydroxide, sodium carbonate, potassium carbonate, sodium hydrogencarbonate, trisodium phosphate, disodium hydrogen phosphate, tripotassium phosphate, dipotassium hydrogen phosphate, triethylamine, pyridine, DBU, DMAP, sodium methoxide, sodium ethoxide, sodium hydride, potassium t-butoxide or sodium t-butoxide.

9. The application of the substituted pyrimidine thioether compound of formula (I) as claimed in claim 1 as an insecticide, an acaricide and/or a bactericide, comprising applying the substituted pyrimidine thioether compound of formula (I) at where in need of.

10. An insecticidal and/or bactericidal composition, wherein the composition comprises the substituted pyrimidine thioether compound of formula (I) as claimed in claim 1 and agriculturally acceptable carriers, wherein the mass fraction of the substituted pyrimidine thioether compound of formula (I) is ranging from 1% to 90%.

* * * * *